(12) United States Patent
Gengrinovitch

(10) Patent No.: US 8,314,060 B2
(45) Date of Patent: *Nov. 20, 2012

(54) PEPTIDE CONJUGATED ANTI-CANCER PRODRUGS

(75) Inventor: Stela Gengrinovitch, Kfar Hanania (IL)

(73) Assignee: BioSight Ltd., Karmiel (IL)

( * ) Notice: Subject to any disclaimer, the term of this patent is extended or adjusted under 35 U.S.C. 154(b) by 192 days.

This patent is subject to a terminal disclaimer.

(21) Appl. No.: 12/623,859

(22) Filed: Nov. 23, 2009

(65) Prior Publication Data

US 2010/0168019 A1     Jul. 1, 2010

Related U.S. Application Data

(63) Continuation-in-part of application No. 11/555,939, filed on Nov. 2, 2006, now Pat. No. 7,638,127, which is a continuation of application No. 10/382,240, filed on Mar. 5, 2003, now Pat. No. 7,135,547, which is a continuation of application No. PCT/IL01/00839, filed on Sep. 5, 2001.

(60) Provisional application No. 60/229,733, filed on Sep. 5, 2000.

(51) Int. Cl.
*A61K 38/00* (2006.01)

(52) U.S. Cl. ...................................................... 514/1.3

(58) Field of Classification Search ........................ None
See application file for complete search history.

(56) References Cited

U.S. PATENT DOCUMENTS

| 4,489,065 | A | 12/1984 | Walton et al. | 424/180 |
| 5,612,474 | A | 3/1997 | Patel | 536/27.14 |
| 5,795,860 | A | 8/1998 | Witt et al. | 506/9 |
| 6,416,758 | B1 | 7/2002 | Thorpe et al. | 424/145.1 |

FOREIGN PATENT DOCUMENTS

| EP | 0 392 745 A2 | 10/1990 |
| EP | 0 859 058 A2 | 8/1998 |

OTHER PUBLICATIONS

Chen et al (JBC, 1997, 272(12): 8090-8098).*
Arap et al., "Cancer Treatment by Targeted Drug Delivery to Tumor Vasculature in a Mouse Model," Science (1998) 279:377-380.
Brandner et al., "Investigating the effect of VEGF glycosylation on glycosaminoglycan binding and protein unfolding," Biochemical and Biophysical Research Communications (2006) 340:836-839.
Dermer, "Another Anniversary for the War on Cancer," Bio/Technology (1994) 12:320.
Dubowchik et al., "Cathepsin B-Sensitive Dipeptide Prodrugs. 1. A Model Study of Structural Requirements for Efficient Release of Doxorubicin," Bioorganic & Medicinal Chemistry Letters (1998) 8:3341-3346.
Dubowchik et al., "Cathepsin B-Sensitive Dipeptide Prodrugs. 2. Models of Anticancer Drugs Paclitaxel (Taxol®), Mitomycin C and Doxorubicin," Bioorganic & Medicinal Chemistry Letters (1998) 8:3347-3352.
Freshney, "Culture of Animal Cells, A Manual of Basic Technique," Alan R. Liss, Inc., New York (1983) p. 4.
Gura, "Systems for Identifying New Drugs are Often Faulty," Science (1997) 278:1041-1042.
Maeda et al., Cancer (1996) 77(5):858-863.
Ramakrishnan et al., "Vascular Endothelial Growth Factor-Toxin Conjugate Specifically Inhibits KDR/*flk-1*-positive Endothelial Cell Proliferation in Vitro and Angiogenesis in Vivo," Cancer Research (Mar. 1996) 56:1324-1330.
Robinson et al., "The splice variants of vascular endothelial growth factor (VEGF) and their receptors," Journal of Cell Science (Mar. 2001) 114:853-865.
Soyez et al., "The crucial role of spacer groups in macromolecular prodrug design," Advanced Drug Delivery Reviews (1996) 21:81-106.
Walker et al., A pore-forming protein with a protease-activated trigger,: Protein Engineering (1994) 7(1):91-97.

* cited by examiner

*Primary Examiner* — Sean Aeder
(74) *Attorney, Agent, or Firm* — Winston & Strawn LLP

(57) ABSTRACT

The present invention relates to prodrug molecules comprising conjugates of an antiproliferative drug, a protease specific cleavable peptide, and, optionally, a targeting peptide, with the prodrugs being substantially inactive prior to degradation of the cleavable sequence by proteolytic enzymes abundant within or in close proximity to the target cancer cell. Also, pharmaceutical compositions of the conjugates and the use of these compositions for treatment of cancer are disclosed.

21 Claims, 6 Drawing Sheets

US 8,314,060 B2

PEPTIDE CONJUGATED ANTI-CANCER PRODRUGS

CROSS-REFERENCE TO RELATED APPLICATIONS

This application is a continuation-in-part of U.S. application Ser. No. 11/555,939 filed Nov. 2, 2006, now U.S. Pat. No. 7,638,127, which is a continuation of U.S. application Ser. No. 10/382,240 filed Mar. 5, 2003, now U.S. Pat. No. 7,135,547, which in turn is a continuation of International application PCT/IL01/00839 filed Sep. 5, 2001, which in turn claims the benefit of 60/229,733 filed Sep. 5, 2000. The entire content of each application is expressly incorporated herein by reference thereto.

FIELD OF INVENTION

The present invention relates to prodrug molecules comprising conjugates of an antiproliferative drug, a protease specific cleavable peptide, and, optionally, a targeting peptide, said prodrugs being substantially inactive prior to degradation of the cleavable sequence by proteolytic enzymes abundant within or in close proximity to the target cancer cell, to pharmaceutical compositions comprising the conjugates and to the use of these compositions for treatment of cancer.

BACKGROUND OF THE INVENTION

Chemotherapeutic Anti-proliferative Drugs

Anti-proliferative drugs, also known as anti-metabolites, act by inhibiting crucial metabolic processes, and are commonly used in the treatment of diseases involving abnormal cell proliferation, such as tumors. However, the utility of these drugs is severely hampered by their excessive toxicity and adverse side effects on healthy cells of the treated patient. Therefore, it would be advantageous to be able to reduce these adverse effects by the use of a prodrug having decreased toxicity.

The use of prodrugs to impart desired characteristics such as increased bioavailability or increased site-specificity of known drugs is a recognized concept in the state of the art of pharmaceutical development. The use of various blocking groups, which must be removed in order to release the active drug is also known in the background art. Commonly, one or more blocking groups may be attached via an available amine, hydroxyl group or other functional reactive group on the drug to yield an amide or an ester. This type of prodrug may be cleaved by non-specific esterases to release the active principle in a sustained-release fashion over a prolonged period of time compared to the native drug species.

Methotrexate (MTX), for example, is an effective antiproliferative drug commonly used in cancer therapy. It is an analogue of dihydrofolate that inhibits the enzyme dihydrofolate reductase (DHFR), thus depleting intracellular tetrahydrofolate ($FH_4$), which is an essential co-factor required for the de novo synthesis of purine nucleotides.

MTX, Mephalan and Chlorambucil are valuable drugs in the treatment of many rapidly growing tumors, however, their use is limited by the frequency and severity of side effects. Unwanted side effects include toxicity to all rapidly dividing normal cells, such as stem cells in the bone marrow, epithelial cells of the intestinal tract, hair follicle cells, etc.

Another major problem in chemotherapy, which is particularly relevant in the case of anti-metabolites, is inherent or acquired resistance of tumors to cytotoxic drugs. For example, development of resistance to MTX frequently follows prolonged exposure to this drug. Resistance may be due to new mutations induced by the clinical treatment, or to positive selection, by the treatment regimen, of pre-existing resistant mutant cell. Known mechanisms for development of resistance involve impaired transport of MTX into cells, e.g. by mutations in the Reduced Folate Carrier (RFC), over expression of the target enzyme DHFR, or mutations in the enzyme responsible for polyglutamination of reduced folates (FPGS).

A more severe problem in the clinic is the phenomenon of multi-drug resistance (MDR), which is a resistance to a broad spectrum of structurally unrelated cytotoxic drugs. MDR is mediated by transmembrane "pumps", which actively expel chemotherapeutic drugs from the tumor cells. MDR significantly limits the efficacy of many cancer chemotherapy regimens and is a major factor in the failure of cancer chemotherapy.

It would, therefore, be most advantageous to have drug derivatives that are specifically targeted to or selectively active in the diseased cells rather than in the healthy cells, thus reducing undesirable side effects. It would also be desirable to generate new anti-proliferative agents that overcome drug-resistance, as well as agents that are active as cytotoxic drugs but lack or have a reduced ability to provoke MDR phenotype.

For specific cytotoxic drugs it has been suggested that the therapeutic index of such drugs might be increased if the drug is covalently bound to a peptide that would be cleaved in the vicinity of the tumor cells by the action of certain proteases. This approach has been suggested for peptide conjugated Methotrexate (Kuefner et al., 1989) and for Arabinofuranosyl cytosine (ara-C) lipid-peptide-drug conjugates (Menger et al., 1994).

Glycosaminoglycans Binding Proteins

Many different types of cell surface polypeptides or glycoproteins have been utilized for targeting drugs to malignant cells, with various degrees of success.

The use of specific cell surface complex sugars as cell surface markers is much less well developed. In part this is due to the fact that the expression of these structures cannot be followed in terms of gene transcription. In other words, the complex sugars are the product of varying expression of the glycosylation enzymes, and cannot be traced directly as gene products.

Proteoglycans are composed of long, unbranched sugar polymers, called glycosaminoglycans (GAGs), which are covalently linked to a core protein. The proteoglycans constitute the extracellular matrix, such as the cartilage, the basement membranes, and the connective tissue. They are also found on the cell surface (Bernfield, M. et al. 1992). Virtually all epithelia express cell-surface proteoglycans, represented principally by glypicans and syndecans. Glypicans are glycosyl phosphatidyl inositol (GPI)-linked molecules, and bear glycosaminoglycans exclusively of the heparan sulfate type. Syndecans are transmembrane proteins, and are decorated with chondroitin sulfate and with heparan sulfate polymers. Syndecans exhibit a complex pattern of cell and development specific expression, however, the molecular mechanisms responsible for this expression have not been fully explored. It was shown, for example that during wound healing the expression of syndecan-1 and -4 is induced. In the case of glypicans, it was shown that glypican-1 is strongly expressed in human pancreatic cancer, whereas its expression is low in normal pancreas.

A variety of regulatory proteins bind tightly to GAGs, including growth factors, cytokines, chemokines, extracellular matrix proteins, cell adhesion molecules, lipid binding proteins, enzymes, and blood coagulation factors. The role of heparan sulphate proteoglycans (HSPGs) in growth factor signaling has been best characterized with respect to fibroblast growth factors (FGFs), which require the presence of heparan sulfate for high affinity binding to their tyrosine kinase receptors (Yayon, A., et al. 1991). Several other growth factors have been found to exhibit a strong requirement for a HSPG co-receptor in their signaling. These include heparin binding EGF-like growth factor (HB-EGF), hepatocyte growth factor (HGF), vascular endothelial growth factor (VEGF) (Yamada, Y. et al., 1997), PDGF, TGF-beta, and other types of growth factors.

Vascular endothelial growth factors (VEGFs) are mitogens for endothelial cells and are potent angiogenic factors in vivo. VEGF-165 contains the peptide encoded by exon-7 of the VEGF gene, confers on VEGF-165 the ability to bind heparan-sulfate molecules. VEGF-145 contains the peptide encoded by exon-6a of the VEGF gene, enabling VEGF-145 to bind ECM (Poltorak et al., 1997).

Several VEGF tyrosine-kinase receptor types have been characterized, these receptors mediates the mitogenic activity and induced cell migration of VEGF. Other VEGF receptors, neuropilin-1 and neuropilin-2 (Gitay-Goren, H., et al., 1992) bind only to the GAG binding forms of VEGF (VEGF-165, VEGF-145) that have GAG binding peptides (axons 6a or 7) of the VEGF gene. These receptors are highly expressed in cancer cells such as human melanoma and carcinoma, but not expressed in normal melanocytes.

VEGFs play a critical role in the process of tumor angiogenesis. This process is essential for tumor progression and for the subsequent process of tumor metastasis.

VEGF soluble receptors have been suggested as an inhibitor of endothelial cell induced proliferation and angiogenesis (Kendall et al. U.S. Pat. No. 5,712,380).

Among the chemokines that are known to bind to heparin the better characterized are Platelet factor 4 (PF4) (Morgan et al., 1977). PF4 is an anti-angiogenic factor that belongs to the CXC Chemokines family. PF4 binds to several receptors that belong to the CXC receptor (CXCR) family involved in angiogenesis. Kaposi's sarcoma cancer is indicated by uncontrolled angiogenesis that is associated with KSHV (Kaposi's sarcoma associated herpes virus) that produces the CXCR-2 receptor homolog.

Injection of fluorescent PF4 to hamsters showed concentration of PF4 at capillary endothelial cells at sites of active angiogenesis. PF4 is accumulated at high concentrations in extra cellular matrix and basement membrane due to its GAG binding ability.

PF4 can bind cell surface proteoglycans, and can be accumulated in the intracellular compartments (Neufeld at al., personal communication). Peptide from its GAG binding domain inhibited melanoma tumor growth in mice xenograft, though it had no effect on cancer cells in-vitro. CXC chemokines have been suggested as therapeutic molecules in modulating the angiogenic and angiostatic responses (U.S. Pat. No. 5,871,723).

Proteolytic Enzymes and Cancer Cells

Cancer invasion involves a proteolytic degradation of extracellular matrix in the surrounding normal tissue. Excess matrix degradation is one of the hallmarks of cancer, and is an important component of the process of tumor progression (Fidler, I. J., 1997). In order for invasion and metastasis to occur, the tumor cell must bypass the basement membrane by degrading the components of the ECM.

Various proteases, in particular the serine protease plasmin, and a variety of matrix metalloproteinases (MMPs), have been implicated in tumor invasion. Plasmin is formed from the inactive zymogen plasminogen by the plasminogen-activators. Plasminogen is produced in the liver and is present extracellulalrly throughout the body. One of the plasminogen-activators, the urokinase plasminogen activator (uPA), is synthesized as a pro-uPA that binds with high affinity to a cell-surface-bound receptor, the uPA receptor (uPAR). Receptor binding of pro-uPA strongly enhances the overall reaction leading to plasmin formation (Dano, K. et al., 1994). Clinical findings have shown that there are elevated tumor antigen levels of Plasminogen Activator (uPA, tPA) and its receptor uPAR in cancer cells and tumors and it plays a role in tumor invasion and metastasis (Koopman et al., 1998; Schmidt et al., 1997).

The MMPs comprise of a large family of over 20 proteins that can degrade all the known components of the extracellular matrix (Massova, I. et al. 1998). MMPs were identified in the tissues surrounding invasive cancers, and show over expression in malignant tissues.

The human aspartic proteinases include cathepsin D, cathepsin E, pepsinogen A, pepsinogen C, and rennin (Taggart, R. T., 1992). Cathepsins D and E are significantly elevated in various cancers and metastases, hence applied as tumor cell markers of epithelial cancers (Matsue, K. et al., 1996)

Nowhere in the background art is it taught or suggested that it is possible to use peptides as drug carriers useful to target prodrugs to tumors.

SUMMARY OF THE INVENTION

It is an object of this invention to target a drug to malignant cells. It is a further object of the present invention to provide prodrugs that are selectively activated in or near malignant cells. It is still a further object of the present invention to provide a technique for treating a malignant tumor or metastatic cancer by selective activation of such prodrugs in or near malignant cells.

These and yet other objectives are accomplished by the compositions according to the present invention, wherein at least one drug is covalently coupled either directly or by means of an appropriate linker to a peptide moiety, which is specifically cleavable by a protease, which is more abundant in malignant cells or secreted by malignant cells more than normal cells. These compositions are prodrugs, which are specifically released near or in the malignant cells by the action of said protease.

According to currently preferred embodiments these prodrugs further comprise a targeting moiety. More preferably the targetor is a peptide sequence covalently attached to the cleavable peptide.

Advantageously, these prodrugs may further comprise blocking groups or protecting groups to prevent their digestion by nonspecific proteases.

Compositions according to the present invention are prodrugs that may be represented schematically as follows:

Protecting Group-Targetor Peptide-Protease Specific Cleavable Sequence-Linker-Drug (Formula I)

wherein "protection group" denotes any appropriate blocking group on the N-, or -C terminal part, or on the side chain of the peptide sequence, which is capable of blocking the action of exopeptidases or endopeptidases; "targetor peptide" may be absent and denotes any peptide sequence capable of causing preferential accumulation of the prodrug at or near the malignant cells; "Protease specific cleavable sequence" denotes any peptide sequence which comprises a peptide bond cleavable by a specific protease, which is more abundant within or in proximity to the malignant cells; "linker" may be absent and denotes any chemical compound present between the drug and the peptide which may be removed chemically, enzymatically or may decompose spontaneously; and "drug" denotes any cytotoxic, cytostatic or chemotherapeutic drug. It is to be understood that the prodrug according to the present invention is generally pharmacologically substantially inactive until the cytotoxic drug is released from the prodrug.

In a further embodiment, compositions according to the present invention may consist of at least one drug conjugated to the protease cleavable sequence and to the targetor peptide. In another embodiment, compositions according to the present invention may consist of a plurality of drug molecules conjugated to at least one protease cleavable sequence and targetor peptide. The plurality of drug molecules may be the same or different at each occurrence.

The present invention further provides pharmaceutical compositions comprising as an active ingredient a prodrug according to the present invention. Such pharmaceutical compositions may be administered by any suitable route of administration.

The technique for activation of the prodrug comprises the following steps:

a) specifically cleaving a peptide bond within the peptide moiety of the prodrug by a protease;

b) digesting the remaining peptide moiety of the prodrug by means of any nonspecific exopeptidase activity; and in cases where the linker moiety is present, c) releasing the active drug from the linker moiety by decomposition of the drug-linker bond.

Currently more preferred embodiments of the invention comprise a prodrug, wherein the chemotherapeutic drug is selected from a group consisting of Melphalan, Methotraxate, Chlorambucil, Doxorubicin, and 5-Fluorouracil.

Currently most preferred embodiments according to the invention comprise a prodrug selected from the group consisting of Prodrug 1: GAG binding domain of PF4-Protease cleavage site-Melphalan;

Prodrug 2: GAG binding domain of PF4-Protease cleavage site-Methotraxate;

Prodrug 3: GAG binding domain of PF4-Protease cleavage site-Chlorambucil;

Prodrug 6: GAG and extracellular binding domain of VEGF-Protease cleavage site-Chlorambucil;

Prodrug 7: GAG and extracellular binding domain of VEGF-Protease cleavage site-Melphalan.

Currently more preferred embodiments of the invention comprise a prodrug, wherein the release peptide that is susceptible to proteolytic degradation is selected from a group consisting of protease cleavage sites of MMP1, MMP9, cathepsin S, tPA, and uPA:

```
SEQ ID NO 2:
Tyr-Gly-Leu-Leu-Gly-Ile-Ala-Gly-Pro-Pro-Gly-Pro

SEQ ID NO 5:
Ser-Pro-Gly-Arg-Val-Val-Arg-Gly

SEQ ID NO 7:
Val-Arg-Gly
```

Currently more preferred embodiments of the invention comprise a prodrug, wherein the targetor is selected from a group consisting of GAG binding domain of PF4, and GAG and extracellular matrix binding domain of VEGF:

```
SEQ ID NO 1:
Pro-Leu-Tyr-Lys-Lys-Ile-Ile-Lys-Lys-Leu-Leu-Gln-
Ser

SEQ ID NO 4:
Lys-Gly-Lys-Gly-Gln-Lys-Arg-Lys-Arg-Lys-Lys-Ser-
Arg-Tyr-Lys-Ser-Trp-Ser-Val.
```

Currently most preferred embodiments according to the invention comprise a prodrug selected from the group consisting of:

```
SEQ ID NO 3:
Tyr-Gly-Leu-Leu-Gly-Ile-Ala-Gly-Pro-Pro-Gly-Pro-
Pro-Leu-Tyr-Lys-Lys-Ile-Ile-Lys-Lys-Leu-Leu-Gln-
Ser coupled to t-Butoxycarbonyl-N-Melphalan;

SEQ ID NO 3:
Tyr-Gly-Leu-Leu-Gly-Ile-Ala-Gly-Pro-Pro-Gly-Pro-
Pro-Leu-Tyr-Lys-Lys-Ile-Ile-Lys-Lys-Leu-Leu-Gln-
Ser coupled to Di-t-Butoxycarbonyl-N-
Methotrexate;

SEQ ID NO 3:
Tyr-Gly-Leu-Leu-Gly-Ile-Ala-Gly-Pro-Pro-Gly-Pro-
Pro-Leu-Tyr-Lys-Lys-Ile-Ile-Lys-Lys-Leu-Leu-Gln-
Ser coupled to Chlorambucil;

SEQ ID NO 6:
Ser-Pro-Gly-Arg-Val-Val-Arg-Gly-Lys-Gly-Lys-Gly-
Gln-Lys-Arg-Lys-Arg-Lys-Lys-Ser-Arg-Tyr-Lys-Ser-
Trp-Ser-Val coupled to Chlorambucil;

SEQ ID NO 8:
Val-Arg-Gly-Lys-Gly-Lys-Gly-Gln-Lys-Arg-Lys-Arg-
Lys-Lys-Ser-Arg-Tyr-Lys-Ser-Trp-Ser-Val coupled
to t-Butoxycarbonyl-N-Melphalan.
```

While the present invention discloses prodrugs which comprise a targetor peptide, the present invention further discloses prodrugs in which the targetor peptide is absent. Thus, the present invention provides a prodrug comprising a conjugate of at least one antiproliferative drug molecule coupled directly or via a linker to a peptide moiety, the peptide moiety being specifically cleavable by an asparaginyl protease abundant in or secreted by malignant cells, thereby preferentially releasing the antiproliferative drug molecule within or at the malignant cells by the action of the asparaginyl protease. It should be noted that the conjugate is pharmacologically inactive.

According to additional embodiments, the peptide moiety cleavable by the asparaginyl protease consists from two to about fourteen amino acids comprising at least one asparagine. According to further embodiments, the peptide moiety cleavable by the asparaginyl protease consists of 3, alternatively 4, 5, 6, 7, 8, 9, 10, 11, or 12 amino acids comprising at least one asparagine. According to a certain embodiment, the asparaginyl protease is legumain. According to yet further embodiments, the peptide moiety cleavable by legumain consists of up to 14 amino acids and comprises the amino acid sequence X1-X2-X3, wherein X1 is selected from the group consisting of Pro, Thr, Asn, and Ala, X2 is selected from the group consisting of Thr, Pro, Asn, and Ala, and X3 is Asn, the peptide consists up to 14 amino acids. According to still further embodiments, the peptide moiety cleavable by legumain consists of up to 14 amino acids which comprise the amino acid sequence selected from the group consisting of Pro-Thr-Asn (SEQ ID NO:9); Pro-Asn-Asn (SEQ ID NO:10); Pro-Ala-Asn (SEQ ID NO:11); Pro-Pro-Asn (SEQ ID NO:12); Thr-Thr-Asn (SEQ ID NO:13); Thr-Asn-Asn (SEQ ID NO:14); Thr-Ala-Asn (SEQ ID NO:15); Thr-Pro-Asn (SEQ ID NO:16); Asn-Thr-Asn (SEQ ID NO:17); Asn-Asn-Asn (SEQ ID NO:18); Asn-Ala-Asn (SEQ ID NO:19); Asn-Pro-Asn (SEQ ID NO:20); Ala-Thr-Asn (SEQ ID NO:21); Ala-Asn-Asn (SEQ ID NO:22); Ala-Ala-Asn (SEQ ID NO:23); Ala-Pro-Asn (SEQ ID NO:24); Thr-Thr-Asn-Leu (SEQ ID NO:25); Thr-Thr-Asn-Ala (SEQ ID NO:26); Pro-Thr-Asn-Leu (SEQ ID NO:27); Pro-Thr-Asn-Ala (SEQ ID NO:28); Pro-Asn-Asn-Leu (SEQ ID NO:29); Pro-Asn-Asn-Ala (SEQ ID NO:30); Thr-Asn-Asn-Leu (SEQ ID NO:31); and Thr-Asn-Asn-Ala (SEQ ID NO:32). According to yet further embodiments, the peptide moiety cleavable by legumain consists of two amino acids of the amino acid sequence selected from the group consisting of SEQ ID NO:33 to SEQ ID NO:38. According to a certain embodiment, the peptide moiety cleavable by legumain consists of the amino acid sequence as set forth in SEQ ID NOs:9 to 11.

According to further embodiments, the antiproliferative drug is selected from the group consisting of cyclophosphamide, chlorambucil, busulfan, Melphalan, Thiotepa, ifosphamide, Nitrogen mustard, methotrexate, 5-Fluorouracil, cytosine arabinoside, 6-thioguanine, 6-mercaptopurine, doxorubicin, daunorubicin, idorubicin, nimitoxantron, dactinomycin, bleomycin, mitomycin, plicamycin, epipodophyllotoxins vincristin, vinblastin, vindestin, Etoposide, Teniposide, carmustin, lomustin, semustin, streptozocin, adrenocorticorticoids, estrogens, antiestrogens, progestins, aromatase inhibitors, androgens, antiandrogens, dacarbazin, hexamethylmelamine, hydroxyurea, mitotane, procarbazide, cisplastin, and carboplatin. According to certain embodiments, the antiproliferative drug is selected from the group consisting of Melphalan, Methotrexate, Chlorambucil, Doxorubicin, and 5-fluorouracil.

According to yet further embodiments, the prodrug further comprises at least one protecting group coupled to the peptide moiety, the protecting group capable of preventing digestion of said peptide moiety by nonspecific proteases. According to still further embodiments, the protecting group is selected from the group consisting of t-butoxycarbonyl and 9-fluorenylmethoxycarbonyl.

The present invention further provides a method for producing a prodrug, the method comprising the step of linking at least one antiproliferative drug molecule and a peptide moiety, the peptide moiety being specifically cleavable by an asparaginyl protease abundant in or secreted by malignant cells. According to some embodiments, the peptide moiety cleavable by the asparaginyl protease consists of from two to about fourteen amino acids. According to a certain embodiment, the asparaginyl protease is legumain. According to yet further embodiments, the peptide moiety cleavable by legumain consists of two to 14 amino acids comprising the amino acid sequence X1-X2-X3, wherein X1 is selected from the group consisting of Pro, Thr, Asn, and Ala, X2 is selected from the group consisting of Thr, Pro, Asn, and Ala, and X3 is Asn. According to still further embodiments, the peptide cleavable by legumain consists of up to 14 amino acids comprising the amino acid sequence selected from the group consisting of SEQ ID NO:9 to SEQ ID NO:32. According to still further embodiments, the peptide moiety cleavable by legumain consists of two amino acids of the amino acid sequence selected from the group consisting of SEQ ID NO:33 to SEQ ID NO:38. According to a certain embodiment, the peptide moiety cleavable by legumain consists of the amino acid sequence set forth in SEQ ID NOs:9 to 11.

According to some embodiments, the antiproliferative drug to be linked to the peptide moiety cleavable by an asparaginyl protease is selected from the group consisting of cyclophosphamide, chlorambucil, busulfan, Melphalan, Thiotepa, ifosphamide, Nitrogen mustard, methotrexate, 5-Fluorouracil, cytosine arabinoside, 6-thioguanine, 6-mercaptopurine, doxorubicin, daunorubicin, idorubicin, nimitoxantron, dactinomycin, bleomycin, mitomycin, plicamycin, epipodophyllotoxins vincristin, vinblastin, vindestin, Etoposide, Teniposide, carmustin, lomustin, semustin, streptozocin, adrenocorticorticoids, estrogens, antiestrogens, progestins, aromatase inhibitors, androgens, antiandrogens, dacarbazin, hexamethylmelamine, hydroxyurea, mitotane, procarbazide, cisplastin, and carboplatin. According to certain embodiments, the antiproliferative drug to be linked to the peptide moiety cleavable by an asparaginyl protease is selected from the group consisting of Melphalan, Methotrexate, Chlorambucil, Doxorubicin, and 5-fluorouracil.

According to some embodiments, the prodrug to be produced by the method of the present invention further comprises a linker between the antiproliferative drug and the peptide. According to additional embodiments, the prodrug further comprises a protecting group capable of preventing digestion of the peptide moiety by nonspecific proteases. According to particular embodiments, the protecting group is selected from the group consisting of t-butoxycarbonyl and 9-fluorenylmethoxycarbonyl.

DETAILED DESCRIPTION OF THE INVENTION

Figure 1:
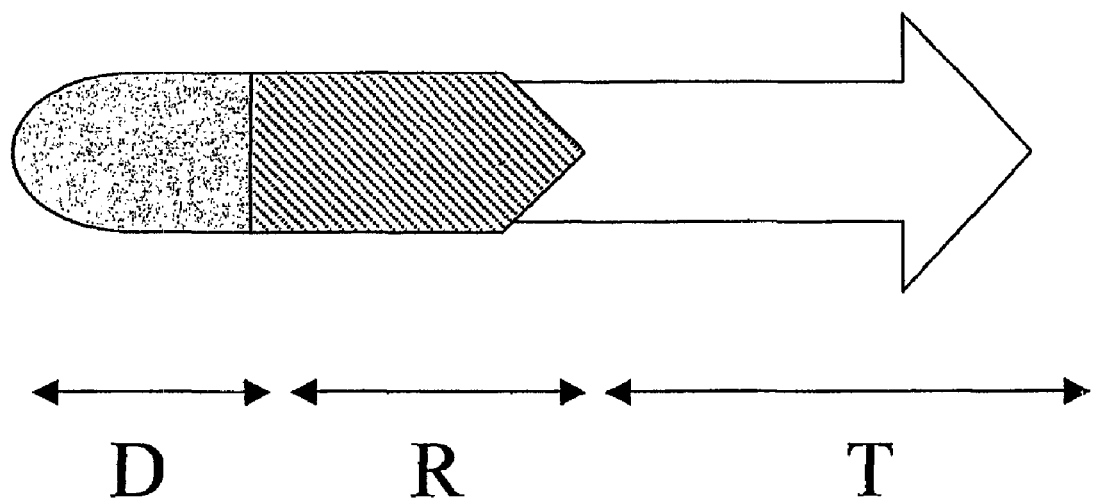
FIG. 1 shows a prodrug model that includes a targeting moiety (T), a protease cleavable moiety (R), and a chemotherapeutic drug (D).

According to the present invention prodrug conjugates are provided which comprise at least one anti-proliferative drug covalently bound to a peptide sequence comprising a peptide bond specifically cleavable by a protease. The peptide sequence further comprises a targeting sequence, designed to increase the localization of the conjugate to the vicinity of the malignant cells. These prodrugs may further comprise linker moieties between the drug and the peptide, and may still further comprise protecting groups or blocking groups attached to the peptide.

In the specification and in the claims the term "drug" denotes any pharmacologically active agent capable of arresting cell growth, or killing the cell in which it is present and includes known cytotoxic, cytostatic or antiproliferative drugs such as are known in the art, exemplified by such compounds as:

Alkaloids: Docetaxel, Etoposide, Irinotecan, Paclitaxel, Teniposide, Topotecan, Vinblastine, Vincristine, Vindesine.

Alkylating agents: Busulfan, Improsulfan, Piposulfan, Benzodepa, Carboquone, Meturedepa, Uredepa, Altretamine, triethylenemelamine, Triethylenephosphoramide, Triethylenethiophosphoramide, Chlorambucil, Chloranaphazine, Cyclophosphamide, Estramustine, Ifosfamide, Mechlorethamine, Mechlorethamine Oxide Hcl, Melphalan, Novemebichin, Perfosfamide Phenesterine, Prednimustine, Trofosfamide, Uracil Mustard, Carmustine, Chlorozotocin, Fotemustine, Lomustine, Nimustine, Semustine Ranimustine, Dacarbazine, Mannomustine, Mitobronitol, Mitolactol, Pipobroman, Temozolomide.

Antibiotics and analogs: Aclacinomycins, Actinomycins, Anthramycin, Azaserine, Bleomycins, Cactinomycin, Carubicin, Carzinophilin, Cromomycins, Dactinomycins, Daunorubicin, 6-Diazo-5-oxo-L-norleucine, Doxorubicin, Epirubicin, Idarubicin, Menogaril, Mitomycins, Mycophenolic Acid, Nogalamycine, Olivomycins, Peplomycin, Pirarubicin, Plicamycin, Porfiromycin, Puromycine, Streptonigrin, Streptozocin, Tubercidin, Zinostatin, Zorubicin.

Antimetabolites: Denopterin, Edatrexate, Methotrexate, Piritrexim, Pteropterin, Tomudex, Trimetrexate, Cladridine, Fludarabine, 6-Mercaptopurine, Pentostatine Thiamiprine, Thioguanine, Ancitabine, Azacitidine, 6-Azauridine, Carmofur, Cytarabine, Doxifluridine, Emitefur, Floxuridine, Fluorouracil, Gemcitabine, Tegafur;

Platinum complexes: Caroplatin, Cisplatin, Miboplatin, Oxaliplatin;

Others: Aceglatone, Amsacrine, Bisantrene, Defosfamide, Demecolcine, Diaziquone, Eflornithine, Elliptinium Acetate, Etoglucid, Etopside, Fenretinide, Gallium Nitrate, Hdroxyurea, Lonidamine, Miltefosine, Mitoguazone, Mitoxantrone, Mopidamol, Nitracrine, Pentostatin, Phenamet, Podophillinic acid 2-Ethyl-Hydrazide, Procarbazine, Razoxane, Sobuzoxane, Spirogermanium, Teniposide Tenuazonic Acid, Triaziquone, 2,2',2"-Trichlorotriethylamine, Urethan.

In the specification and in the claims the term "protease specific sequence" denotes any peptide sequence comprising a sequence cleavable by a specific protease, and includes peptides of from about two to about fourteen amino acids comprising at least one site that is cleaved by a specific protease. More preferred are peptide sequences comprising from about three to about twelve amino acids, as exemplified hereinbelow.

In the specification and in the claims the term "linker" denotes any chemical compound, which may be present between the drug moiety and the peptide moiety of the prodrug. This linker may be removed from the drug by chemical means, by enzymatic means, or spontaneously. The linker may be pharmacologically inert or may itself provide added beneficial pharmacological activity. The term "spacer" may also be used interchangeably as a synonym for linker.

In the specification and in the claims the term "protection group" denotes any appropriate blocking group on the N-, or -C terminal part, or on the side chain of the peptide sequence, which is capable of blocking the action of exopeptidases or endopeptidases, such as are well known in the art.

The protection group may itself be pharmacologically inert or may provide added pharmacologically beneficial attributes to the conjugate. Most advantageously the protecting group will be lipophilic, thereby improving the ability of the conjugate to penetrate into cells.

The prodrug includes several moieties: an optional targeting moiety, consisting of a targetor peptide that recognizes cancer cells or malignant tissues, a protease specific cleavable moiety, consisting of a cleavable sequence recognized by degrading enzymes that are more abundant within or in proximity to the malignant cells, and a chemotherapeutic drug (FIG. 1).

Figure 2:
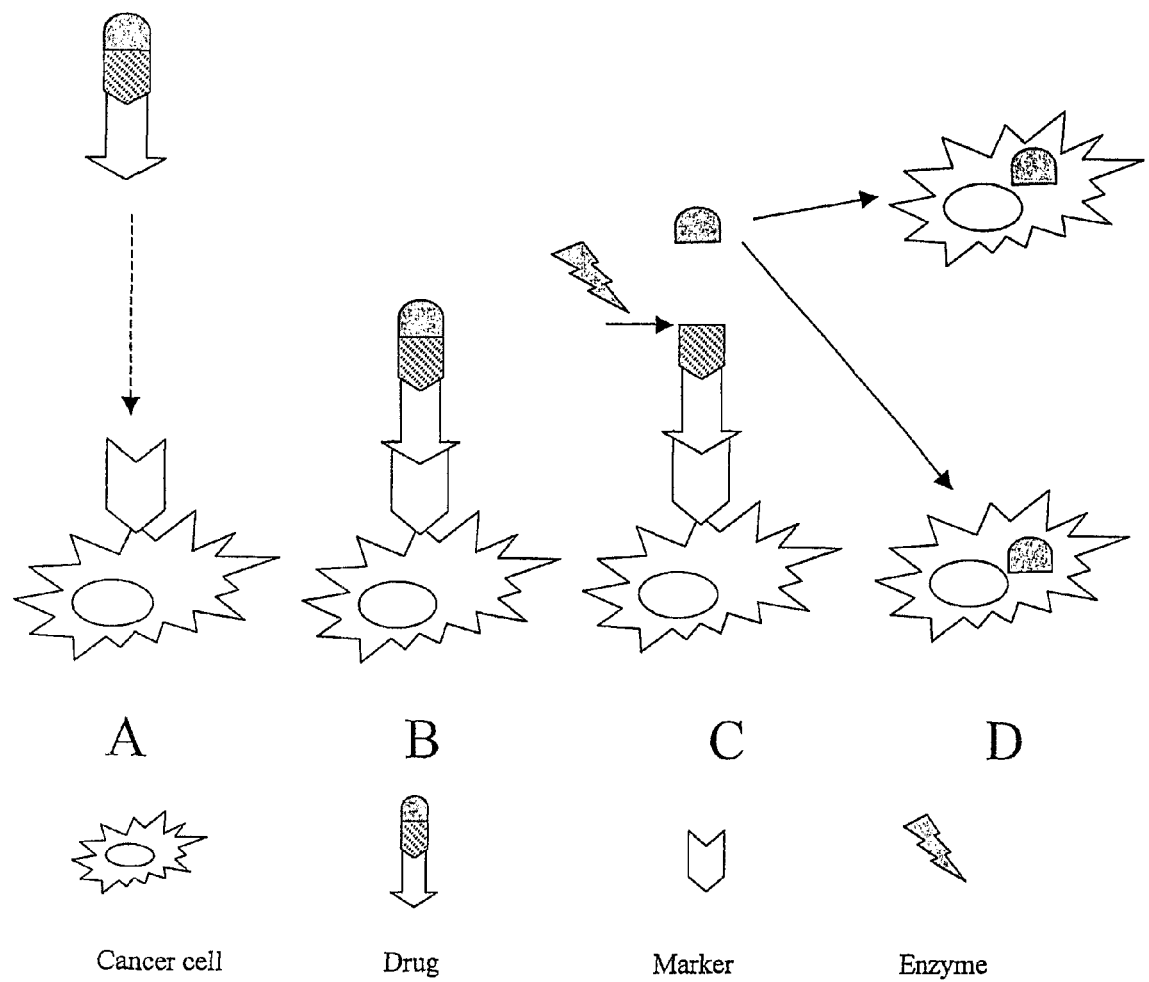
FIG. 2 shows a model of an extracellular prodrug activation that includes the targeting of a prodrug to a marker present on a cancer cell, and the release of the chemotherapeutic drug from its carrier by a specific extracellular degrading enzyme.
Figure 3:
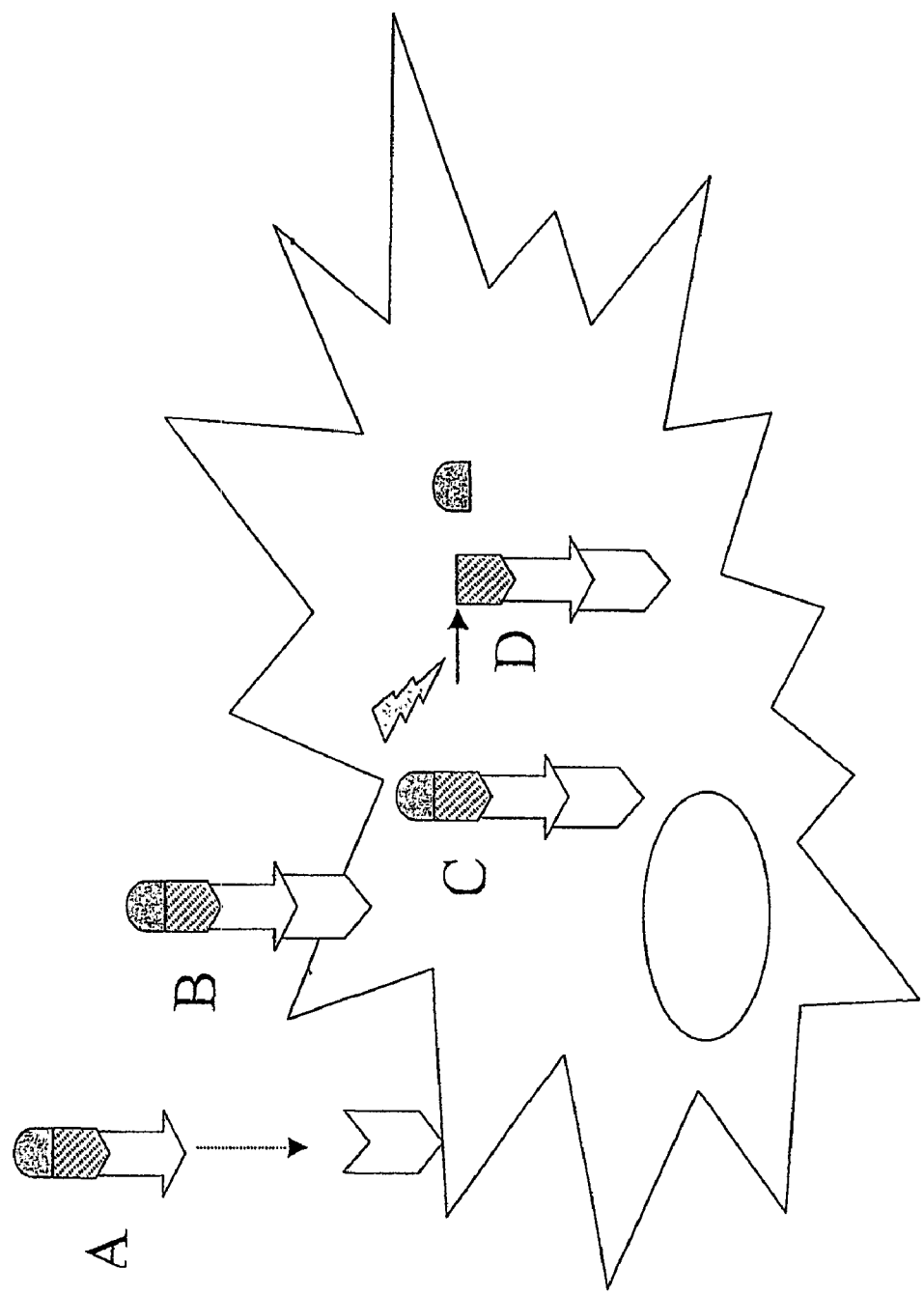
FIG. 3 depicts a model of an intracellular prodrug activation that includes the targeting of a prodrug to a marker present on a cancer cell, the internalization of the prodrug-marker complex into the cell, and the release of the chemotherapeutic drug from its carrier by a specific intracellular degrading enzyme.

The prodrug may act on cancer cells and tissues by several concurrent mechanisms as follows: (i) The extracellular prodrug activation—the prodrug is targeted to a cancer cell, which displays a cancer specific marker recognized by the targeting moiety (FIG. 2A), the targeting moiety binds to the marker (FIG. 2B), the chemotherapeutic drug is released from the carrier by a specific extracellular degrading enzyme (FIG. 2C), and the chemotherapeutic drug attacks the cancer cell (FIG. 2D); (ii) The intracellular prodrug activation—the prodrug is targeted to a cancer cell, which displays a cancer specific marker recognized by the targeting moiety (FIG. 3A), the targeting moiety binds to the marker (FIG. 3B), the prodrug-marker complex are internalized into the cell (FIG. 3C), the chemotherapeutic drug is released from the carrier by a specific intracellular degrading enzyme, and the chemotherapeutic drug attacks the cancer cell (FIG. 3D).

In prodrugs according to the invention, the drug could be placed at either the N-terminal or C-terminal side of the peptide. The skilled artisan will be able to optimize the appropriate linkage and position of the drug moiety within the prodrug. Various concerns should be taken into consideration to guide the artisan in this decision, such as selection of the peptide sequence, selection of the linker, selection of the position of attachment to the drug species, and requirements concerning host intracellular enzymes for drug activation.

The principles that apply to the selection of peptide, linker, attachment site, etc., will be detailed herein for exemplary compounds. The principles may be generalized as follows:

a) Selection of the peptide sequence: any peptide sequence that is cleavable by a protease that is more abundant within or in proximity to cancer cells may be suitable.

b) Selection of the linker: any chemical moiety that can serve as a linker between the peptide and the drug. The linker may be cleaved by chemical reaction, enzymatic reaction, or spontaneously. The linker may also serve for optimizing the specificity of the peptide-protease interaction.

c) Selection of the position of attachment to the drug species: the drug may be attached to either one or to both sides of the peptides, according to the peptidase activities that exists in the targeted cells.

d) Selection of the protecting group: The protecting group may be any chemical moiety that reduces the non-specific prodrug degradation (to active or inactive compounds). Advantageously, the protecting group can be a compound that increases the selectivity of the prodrug towards the cancer cells or tissues, or a compound that increases the permeability of the prodrug towards the cancer cells or tissues. According to a second embodiment of the invention, the protecting group can itself be replaced by a second drug or a second molecule of the same drug.

e) Selection of the drug: the drug can be any anti-proliferative, cytotoxic or cytostatic agent. It may be released in protected or unprotected form, i.e., it can itself be a prodrug. For instance, the targetor moiety may be cleaved extracellularly and the resultant drug-linker conjugate may still be a prodrug that releases the active drug species intracellularly for effective treatment of oncogenesis.

Selection of the Chemotherapeutic Drug

Chemotherapeutic drugs have different ways in which they inhibit cancer. Chemotherapeutic drugs can damage the DNA template by alkylation, by cross-linking, or by double-strand cleavage of DNA. Other cancer drugs can block RNA synthesis by intercalation. Some agents are spindle poisons, such as vinca alkaloids, or anti-metabolites that inhibit enzyme activity, or hormonal and anti-hormonal agents. Chemotherapeutic drugs for targeting may be selected from various groups of agents, including but not limited to alkylating agents, antimetabolites, antitumor antibiotics, vinca alkaloids, epipodophyllotoxins, nitrosoureas, hormonal and anti-hormonal agents, and toxins.

Currently more preferred alkylating agents may be exemplified by cyclophosphamide, chlorambucil, busulfan, Melphalan, Thiotepa, ifosphamide, Nitrogen mustard.

Currently more preferred antimetabolites may be exemplified by methotrexate, 5-Fluorouracil, cytosine arabinoside, 6-thioguanine, 6-mercaptopurin.

Currently more preferred antitumor antibiotics may be exemplified by doxorubicin, daunorubicin, idorubicin, nimitoxantron, dactinomycin, bleomycin, mitomycin, plicamycin.

Currently more preferred vinca alkaloids and epipodophyllotoxins may be exemplified by vincristin, vinblastin, vindestin, Etoposide, Teniposide.

Currently more preferred nitrosoureas may be exemplified by carmustin, lomustin, semustin, streptozocin.

Currently more preferred hormonal and antihormonal agents may be exemplified by adrenocorticoids, estrogens, antiestrogens, progestins, aromatas inhibitors, androgens, antiandrogens.

Additional preferred random synthetic agents may be exemplified by dacarbazin, hexamethylmelamine, hydroxyurea, mitotane, procarbazide, cisplastin, carboplatin.

Selection of the Targeting Sequence

The targeting sequences for the chemotherapeutic drug may be a glycosaminoglycan binding domain, or other binding domain found on the cancer cells or tissues.

In this invention the selection of a specific glycosaminoglycan binding domain as a targeting sequence was made by structure analysis of specific glycosaminoglycan chains present on the cancer cells or tissues. Since different cell types have been shown to synthesize proteoglycans with different glycosaminoglycan structures and functions, such differences may be utilized for the selection of targetor peptide.

The selection of specific glycosaminoglycan binding domains for targeting can be carried out by different means, for example, by screening for native glycosaminoglycan binding domains capable of interacting with the specific glycosaminoglycans found on cancer cells or tissues. Alternatively, this selection can be carried out by screening for specific peptides (in peptide libraries) that interact with the specific glycosaminoglycans found on cancerous cells or tissues.

Native specific glycosaminoglycan binding domains for targeting can be selected from glycosaminoglycan binding proteins, exemplified but not limited to growth factors including but not limited to fibroblast growth factors (1-23), epidermal growth factors, platelet derived growth factors, vascular endothelial growth factors, cytokines and chemokines including but not limited to interleukins, PF4, GRO-alpha, GRO-beta, GRO-gamma, extracellular matrix and cell adhesion proteins including but not limited to fibronectin, collagen, laminin, thrombospondin, integrins, N-CAM, PECAM, CD44, lipid binding proteins including but not limited to lipoprotein lipase, apolipoprotein B and E, LDL, enzymes including but not limited to acetylcholinesterase, GAG degrading enzymes, blood coagulation factors including but not limited to antithrombin III tissue factor, and other proteins including but not limited to influenza virus, Diphteria toxin, prion proteins, some of them involve in various malignancies.

Selection of the Release Sequence

Cancer invasion involves a proteolytic degradation of the extracellular matrix of the surrounding normal tissue. Excess matrix degradation is one of the hallmarks of cancer, and is an important component of the process of tumor progression (Fidler, I. J., 1997). When a tumor cell acquires the ability to invade and destroy a normal tissue, it is termed malignant. The ability to form tumor metastases is characteristic of highly malignant cancers with poor clinical outcome. In order to invade and metastasize, the tumor cell must bypass the basement membrane by degrading the components of the extracellular matrix. During the invasion, the tumor cell penetrates the basement membrane underlying the tumor. It then moves through more extracellular matrix to reach the circulation either through the lymphatic- or through the blood vessels. The process of entering the blood stream is termed intravasation. In order to establish itself at a distant site, the cancer cell repeats the entire process in reverse. During this process of extravasation the tumor cell leaves the blood circulation, and penetrates the host tissue, again crossing through a basement membrane. If the tumor cells are capable of growing in this unfamiliar environment, clinically significant metastases are formed and can pose a threat to the life of the host.

Various proteases have been implicated in tumor invasion. In particular, the serine protease plasmin, the MMPs, and the aspartic proteinases have been shown to be involved in this process.

The MMPs comprise of a large family of over 20 proteins that can degrade all the known components of the extracellular matrix (Massova I. et al. 1998). These proteinases demonstrate some selectivity such that an individual MMP has the ability to degrade a particular subset of matrix proteins. MMPs were identified in the tissues surrounding invasive cancers, and show over expression in malignant tissues.

The human aspartic proteinases include cathepsin D, cathepsin E, pepsinogen A, pepsinogen C, and renin. Cathepsins D and E are significly elevated in various cancers and metastases, hence applied as tumor cell markers of epithelial cancers.

In the present invention specific protease cleavable sequences were selected by structure analysis of specific biodegradable sequences that are degraded by proteases that are more abundant within or in proximity to the malignant cells. The proteases are grouped as follows:

Matrix metalloproteinases may be exemplified but not limited to collagenases, gelatinases, stromelysins.

Aspartic proteases may be exemplified but not limited to cathepsin D, cathepsin E, pepsinogen A, pepsinogen C, renin.

Serine proteases may be exemplified but not limited to plasmin, tissue-type plasminogen activator (tPA), urokinase-type plasminogen activator (uPA).

Cysteine proteases may be exemplified but not limited to cathepsin B, cathepsin L, cathepsin S.

Asparaginyl proteases may be exemplified but not limited to legumain.

The protease specific cleavable sequences can be selected by screening for native degradation substrates of proteases, which are more abundant within or in proximity to malignant cells. Alternatively, the protease specific cleavable sequences can be selected by screening for specific peptides (in peptide libraries) that can be susceptible to a proteolytic degradation by proteases, which are more abundant within or near malignant cells.

Native specific biodegradable sequences can be selected from the groups of native substrates as listed below:

Matrix metalloproteinases substrates exemplified but not limited to collagens, gelatins, fibronectin, elastin, laminin, proteoglycans, serpin, uPA.

Aspartic proteases substrates exemplified but not limited to Bioactive peptides, Beta-amyloid precursor.

Serine proteases substrates exemplified but not limited to plasminogen, fibrin, PAR1 thrombin receptor, uPAR-1 (uPA receptor).

Cysteine proteases substrates exemplified but not limited to collagens.

Asparaginyl proteases substrates exemplified but not limited to antigenic proteins for MHC class II, proenzymes (see, for example, Chen J. M. et al., J. Biol. Chem. 272: 8090-8098, 1997; and Dando P. M. et al., Biochem J. 339: 743-749, 1999).

Currently most preferred embodiments of the invention comprise a conjugate, wherein the chemotherapeutic drug is selected from a group consisting of Melphalan, Methotraxate, Chlorambucil, Doxorubicin, 5-Fluorouracil, folic acid, and N—N'-Diethylaminobezoic acid.

Currently most preferred embodiments encompass the following conjugates:

Prodrug 1: GAG binding domain of PF4-Protease cleavage site-Melphalan

Prodrug 2: GAG binding domain of PF4-Protease cleavage site-Methotraxate.

Prodrug 3: GAG binding domain of PF4-Protease cleavage site-Chlorambucil.

Prodrug 4: GAG binding domain of PF4-Protease cleavage site-folic acid.

Prodrug 5: GAG binding domain of PF4-Protease cleavage site-N—N'-Diethylaminobezoic acid.

Prodrug 6: GAG and extracellular binding damain of VEGF-Protease cleavage site-Chlorambucil.

Prodrug 7: GAG and extracellular binding damain of VEGF-Protease cleavage site-Melphalan Prodrug 8: Asparaginy Protease cleavage site-Methotraxate Prodrug 9: Asparaginy Protease cleavage site-Doxorubicin Prodrug 10: Asparaginy Protease cleavage site-5-Fluorouracil.

Currently most preferred embodiments of the invention comprise a prodrug, wherein the protease cleavable peptide that is susceptible to proteolytic degradation is selected from a group consisting of protease cleavage sites of MMP1, MMP9, cathepsin S, tPA, uPA, and asparaginyl proteases:

SEQ ID NO 2:
Tyr-Gly-Leu-Leu-Gly-Ile-Ala-Gly-Pro-Pro-Gly-Pro

SEQ ID NO 5 is:
Ser-Pro-Gly-Arg-Val-Val-Arg-Gly

SEQ ID NO 7 is:
Val-Arg-Gly

Currently most preferred embodiments of the invention comprise a prodrug, wherein the targetor is selected from a group consisting of GAG binding domain of PF4, and GAG and extracellular matrix binding domain of VEGF:

SEQ ID NO 1:
Pro-Leu-Tyr-Lys-Lys-Ile-Ile-Lys-Lys-Leu-Leu-Gln-Ser

SEQ ID NO 4 is:
Lys-Gly-Lys-Gly-Gln-Lys-Arg-Lys-Arg-Lys-Lys-Ser-Arg-Tyr-Lys-Ser-Trp-Ser-Val

Currently the specific embodiments of the present invention consist of prodrugs composed of:

SEQ ID NO 3:
Tyr-Gly-Leu-Leu-Gly-Ile-Ala-Gly-Pro-Pro-Gly-Pro-Pro-Leu-Tyr-Lys-Lys-Ile-Ile-Lys-Lys-Leu-Leu-Gln-Ser coupled to t-Butoxycarbonyl-N-Melphalan;

SEQ ID NO 3:
Tyr-Gly-Leu-Leu-Gly-Ile-Ala-Gly-Pro-Pro-Gly-Pro-Pro-Leu-Tyr-Lys-Lys-Ile-Ile-Lys-Lys-Leu-Leu-Gln-Ser coupled to Di-t-Butoxycarbonyl-N-Methotrexate;

SEQ ID NO 3:
Tyr-Gly-Leu-Leu-Gly-Ile-Ala-Gly-Pro-Pro-Gly-Pro-Pro-Leu-Tyr-Lys-Lys-Ile-Ile-Lys-Lys-Leu-Leu-Gln-Ser coupled to Chlorambucil;

SEQ ID NO 6:
Ser-Pro-Gly-Arg-Val-Val-Arg-Gly-Lys-Gly-Lys-Gly-Gln-Lys-Arg-Lys-Arg-Lys-Lys-Ser-Arg-Tyr-Lys-Ser-Trp-Ser-Val coupled to Chlorambucil;

SEQ ID NO 8:
Val-Arg-Gly-Lys-Gly-Lys-Gly-Gln-Lys-Arg-Lys-Arg-Lys-Lys-Ser-Arg-Tyr-Lys-Ser-Trp-Ser-Val coupled to t-Butoxycarbonyl-N-Melphalan According to some embodiments, the prodrug is devoid of a targetor peptide, the asparaginyl protease of the prodrug is legumain, and the peptide moiety cleavable by legumain consists of known amino acid sequences (see, for example, Chen J. M. et al., J. Biol. Chem. 272: 8090-8098, 1997; and Dando P. M. et al., Biochem J. 339: 743-749, 1999). According to exemplary embodiments, the peptide cleavable by legumain is selected from the group consisting of:

| | |
|---|---|
| Pro-Thr-Asn; | (SEQ ID NO: 9) |
| Pro-Asn-Asn; | (SEQ ID NO: 10) |
| Pro-Ala-Asn; | (SEQ ID NO: 11) |
| Pro-Pro-Asn; | (SEQ ID NO: 12) |
| Thr-Thr-Asn; | (SEQ ID NO: 13) |
| Thr-Asn-Asn; | (SEQ ID NO: 14) |
| Thr-Ala-Asn; | (SEQ ID NO: 15) |
| Thr-Pro-Asn; | (SEQ ID NO: 16) |
| Asn-Thr-Asn; | (SEQ ID NO: 17) |
| Asn-Asn-Asn; | (SEQ ID NO: 18) |
| Asn-Ala-Asn; | (SEQ ID NO: 19) |
| Asn-Pro-Asn; | (SEQ ID NO: 20) |
| Ala-Thr-Asn; | (SEQ ID NO: 21) |

```
Ala-Asn-Asn;         (SEQ ID NO: 22)

Ala-Ala-Asn;         (SEQ ID NO: 23)

Ala-Pro-Asn;         (SEQ ID NO: 24)

Thr-Thr-Asn-Leu;     (SEQ ID NO: 25)

Thr-Thr-Asn-Ala;     (SEQ ID NO: 26)

Pro-Thr-Asn-Leu;     (SEQ ID NO: 27)

Pro-Thr-Asn-Ala;     (SEQ ID NO: 28)

Pro-Asn-Asn-Leu;     (SEQ ID NO: 29)

Pro-Asn-Asn-Ala;     (SEQ ID NO: 30)

Thr-Asn-Asn-Leu;     (SEQ ID NO: 31)
and

Thr-Asn-Asn-Ala.     (SEQ ID NO: 32)
```

According to additional embodiments, the peptide cleavable by legumain consists of two amino acids (see, for example, Chen J. M. et al., J. Biol. Chem. 272: 8090-8098, 1997; and Dando P. M. et al., Biochem J. 339: 743-749, 1999). The amino acid sequence of the peptide cleavable by legumain is thus selected from the group consisting of:

```
Asn-Lys;             (SEQ ID NO: 33)

Asn-Leu;             (SEQ ID NO: 34)

Asn-Ala;             (SEQ ID NO: 35)

Asn-Glu;             (SEQ ID NO: 36)

Asn-Asp;             (SEQ ID NO: 37)
and

Asn-Asn.             (SEQ ID NO: 38)
```

According to certain embodiments, the prodrug is composed of:
SEQ ID NO 9: Pro-Thr-Asn coupled to Methotrexate
SEQ ID NO 10: Pro-Asn-Asn coupled to Doxorubicin
SEQ ID NO 11: Pro-Ala-Asn coupled to 5-Fluorouracil.

Although the invention will now be described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

EXAMPLE 1

Synthesis of t-Butoxycarbonyl-N-Melphalan 100 mg Melphalan were dissolved in 0.56 ml water solution of NaOH (0.44 g in 11 ml HPLC water). The solution was mixed and 0.25 ml of t-butyl alcohol was added. 0.08 ml of di-tert-butylcarbonate was added to the mixture and mixed for 1.5 hours.

The product t-Butoxycarbonyl-Melphalan was extracted by Hexane and precipitated by 0.1N HCl. The precipitate was washed with HPLC water and dissolved in Ethanol. Purified t-Butoxycarbonyl-N-Melphalan was crystallized from Ethanol.

Purity of t-Butoxycarbonyl-N-Melphalan was analyzed using reversed-phase high performance liquid chromatography (HPLC) on LiChroCART 250-4 HPLC cartridge Purospher RP-18 (purchased from Merck).

The molecular weight and chemical structure of the product were analyzed by Mass spectrometry on matrix assisted laser desorption ionization (MALDI) or electrospray ionization (ESI), interfaced to quadruple ion trap and TOF (time of flight) mass spectrometer.

EXAMPLE 2

Synthesis of 9-Fluorenylmethoxycarbonyl-N-Melphalan 0.5 mmol Melphalan and 0.7 mmol 9-fluorenylmethelsuccinimidyl-carbonate were dissolved in 5 ml of acetonitrile/water solution (2/1). The solution was mixed and 0.1 ml of diisopropylethylamine was added. The mixture was stirred for 20 hours.

Acetonitrile was evaporated. The product 9-fluorenylmethelcarbonyl-Melphalan was extracted by Ethylacetate/5% citric acid. The organic layer was washed with 5% citric acid and then evaporated to dryness. The product was dissolved in Ethanol. Purified 9-fluorenylmethelcarbonyl-N-Melphalan was crystallized from Ethanol.

Purity, molecular weight and chemical structure of 9-fluorenylmethelcarbonyl-N-Melphalan were analyzed using reversed-phase HPLC, and Mass spectrometry as described in Example 1.

EXAMPLE 3

Synthesis of Di-t-Butoxycarbonyl-N-Methotrexate 0.5 mmol Methotrexate (N-[4-[[(2,4-diamino-6-pteridinyl)-methylamino]benzoyl]-L-glutamic acid) and 1.5 mmol of triethylamine were dissolved in 5 ml HPLC water. The solution was mixed and 1.1 mmol of S-Boc-2-mercapto-4,6-dimethyl-pirimidine dissolved in 5 ml of dioxane was added. The reaction mixture was mixed for 18 hours. The product Di-t-Butoxycarbonyl-N-Methotrexate was extracted by Ethylacetate and saturated with citric acid solution. The organic layer was washed with saturated citric acid solution and saturated NaCl solution and then evaporated to dryness. The product was dissolved in Ethanol. Purified Di-t-Butoxycarbonyl-N-Methotrexate was crystallized from Ethanol/ice cold water solution.

Purity, molecular weight and chemical structure of Di-t-Butoxycarbonyl-N-Methotrexate were analyzed using reversed-phase HPLC, and Mass spectrometry as described in Example 1.

EXAMPLE 4

Synthesis of Peptide Carrier I (T-R)

The peptide carrier for the chemotherapeutic drug was synthesized by using combinatorial chemistry and solid phase peptide synthesis. Fmoc/Boc protected amino acids were used for the synthesis.

The first amino acid was bound to activated solid support such as polystyrene beads onto which hydroxybenzyl alcohol linker has been attached (Wang, 1973).
Synthesis of the peptide carrier I (SEQ ID NO 3) containing targeting (SEQ ID NO 1) and cleavable (SEQ ID NO 2) domains (T-R) was as follows:

```
Targeting (T) peptide sequence (SEQ ID NO 1) is:
Pro-Leu-Tyr-Lys-Lys-Ile-Ile-Lys-Lys-Leu-Leu-Gln-
Ser Cleavable (R) peptide sequence (SEQ ID NO 2) is:
Tyr-Gly-Leu-Leu-Gly-Ile-Ala-Gly-Pro-Pro-Gly-Pro
```

The first amino acid Fmoc-Ser(But)-OH was coupled to Wang resin (Wang, 1973)
By using Dichlorobenzoylchloride method: 1 g of Wang resin was swollen in 8 ml of dimethylformamid (DMF) for 30 minutes. The resin was washed 5 times with DMF. Two equivalents of Fmoc-Ser(But)-OH were dissolved in 8 ml DMF, and added to the resin. The resin was shaked for 30 minutes at room temperature. 3.3 equivalents of Pyridine and 2 equivalents of 2,6-Dichlorobenzoylchloride were added to the resin and the resin was shaked for 20-24 hours. The resin was washed on a filter glass with DMF and 1,2-Dichloroethane (DCE). The remaining hydroxyl groups of the resin were benzoylated with Benzoyl chloride (0.3 ml) and Pyridine (0.3 ml) in 8 ml DCE for 2 hours at room temperature. The resin was washed on a filter glass with DMF and with methanol, and dried in vacuum over silica gel.

At the end of the coupling the Fmoc-Ser(But)-Resin was deprotected by piperidine method: 1 g resin with 0.5 mmol Fmoc-amino acid was deprotected 4 times with 10 ml of 20%-50% Piperidine in NMP or DMF. Deprotection was monitored by spectrophotometer measuring the level of the free Fmoc residue at 290 nm of each deprotection step. At the end of deprotection the resin was washed 10 times with DMF and methanol, and a sample of the resin beads was analyzed by Kaiser test (Kaiser et al., 1970).

The next amino acids were bound to the peptide-resin by subsequent steps of deprotection and coupling made for the extension of the peptide on the resin using DIC/HOBt method: Fmoc-amino acid was dissolved in NMP or DMF for 3 minutes and reactivated with DIC/HOBt (molar ratio 1:1:1 to amino acid) for 20 minutes. Coupling of amino acid to peptide-resin was made for 60 minutes at room temperature with mechanical mixing and nitrogen bubbling.

At the end of peptide synthesis cleavage of the peptide from the resin was made using TFA and scavengers (10-20 ml for 1 g peptide-resin) for 1-4 hours mixing at room temperature. The eluate was filtered from the resin, the resin was washed 2 times with TFA, and the filtrates were combined. Most of the TFA was evaporated from the elution, and peptide was precipitated from TFA using ice-cold diisopropyl-ether. The peptide precipitate was washed 3 times with ice-cold diisopropyl ether, and then evaporated. The peptide was dissolved in water or buffer and lyophilized.

The peptide was analyzed using reversed-phase HPLC, mass spectrometry, and gel electrophoresis separation.

HPLC was made on LiChroCART 250-4 HPLC cartridge LiChrospher WP 300 RP-18 (5 micrometer) (purchased from Merck). The prodrug was separated on HPLC using a gradient of 20% B to 100% B at flow rate of 0.5 ml/min, and the product was detected at 214 nm (Fluent A: water+0.1% TFA, Fluent B: Acetonitrile+10% water+0.1% TFA).

Mass spectrometry was made by matrix assisted laser desorption ionization (MALDI) or electrospray ionization (ESI), interfaced to quadruple ion trap and TOF (time of flight) mass spectrometer.

Gel electrophoresis was made on Tris-Tricin/SDS 10%-20% gradient gels (purchased from Bio-Rad).

EXAMPLE 5

Synthesis of Peptide Carrier II

Synthesis of the Peptide Carrier II (SEQ ID NO 6) Containing Targeting (SEQ ID NO 4) and Cleavable (SEQ ID NO 5) Domains (T-R)

```
Targeting (T) peptide sequence (SEQ ID NO 4) is:
Lys-Gly-Lys-Gly-Gln-Lys-Arg-Lys-Arg-Lys-Lys-Ser-
Arg-Tyr-Lys-Ser-Trp-Ser-Val Cleavable (R) peptide sequence (SEQ ID NO 5) is:
Ser-Pro-Gly-Arg-Val-Val-Arg-Gly
```

The first amino acid Fmoc-Val-OH was coupled to Wang resin (Wang, 1973) by using Dichlorobenzoylchloride method as described in example 4.

At the end of the coupling the Fmoc-Val-Resin was deprotected by DBU method: 1 g resin with 0.5 mmol Fmoc-amino acid was deprotected 4 times with 10 ml of 2% 1,8-diazabicyco[5.4.0]undec-7-ene (DBU) and 2% Piperidine in NMP or DMF. At the end of deprotection a sample of the resin beads was analyzed by Kaiser test.

The next amino acids were bound to the peptide-resin by subsequent steps of deprotection and coupling made for the extension of the peptide on the resin using DIC/HOBt method as described in Example 4 or HBTU/HOBt method: Fmoc-amino acid was dissolved in NMP or DMF for 3 minutes, reactivated with HOBt (molar ratio 1:1 to amino acid) for 3 minutes and transferred to the peptide-resin. HBTU (molar ratio 1:1 to amino acid) was added for 5 minutes and DIPEA (molar ratio 2:1 to amino acid) was added. Coupling of amino acid to peptide-resin was made for 120 minutes at room temperature with mechanical mixing and nitrogen bubbling.

Peptide cleavage and side chain deprotection was made as described in example 4.

The peptide was analyzed using reversed-phase HPLC, mass spectrometry, and gel electrophoresis separation as described in example 4.

EXAMPLE 6

Synthesis of Peptide Carrier III

Synthesis of the Peptide Carrier III (SEQ ID NO 8) Containing Targeting (SEQ ID NO 4) and Cleavable (SEQ ID NO 7) Domains (T-R)

```
Targeting (T) peptide sequence (SEQ ID NO 4) is:
Lys-Gly-Lys-Gly-Gln-Lys-Arg-Lys-Arg-Lys-Lys-Ser-
Arg-Tyr-Lys-Ser-Trp-Ser-Val Cleavable (R) peptide sequence (SEQ ID NO 7) is:
Val-Arg-Gly
```

The first amino acid Fmoc-Val-OH was coupled to Rink resin. One gram of Rink resin was swollen in 10 ml of DMF for 1 hour. The resin was washed 5 times with DMF. Resin was deprotected 4 times with 20% Piperidine in NMP. Deprotection was monitored by spectrophotometer measuring the level of the free Fmoc residue at 290 nm. At the end of deprotection the resin was washed 10 times with NMP, methanol, NMP, and a sample of the resin beads was analyzed by Kaiser test (Kaiser et al 1970).

Amino acids were bound to the peptide-resin by subsequent steps of deprotection and coupling made for the extension of the peptide on the resin using HBTU/HOBt method or TBTU/HOBt method: Fmoc-amino acid was dissolved in NMP or DMF for 3 minutes, reactivated with HOBt (molar ratio 1:1 to amino acid) for 3 minutes and transferred to the peptide-resin. TBTU (molar ratio 1:1 to amino acid) was added for 5 minutes and DIPEA (molar ratio 3:1 to amino acid) was added. Coupling of amino acid to peptide-resin was made for 120 minutes at room temperature with mechanical mixing and nitrogen bubbling.

At the end of peptide synthesis cleavage of the peptide from the resin was made using 2 step cleavage method: 20%-50% TFA in DCM and scavengers (10-20 ml for 1 g peptide-resin) for 15-30 minutes mixing at room temperature. The elution was filtered from the resin, the resin was washed 2 times with 20% TFA/DCM, and filtrates were combined. Most of the liquid was evaporated from the elution, and 95% TFA and 5% scavengers were added to the elute for 1-4 hours of deprotection.

Peptide was precipitated from TFA using ice-cold t-butyl-methyl-ether. The peptide precipitate was washed 3 times with ice-cold t-butyl-methyl-ether, and then evaporated. The peptide was dissolved in water or buffer and lyophilized.

The peptide was analyzed using reversed-phase HPLC, mass spectrometry, and gel electrophoresis separation as described in Example 4.

EXAMPLE 7

Synthesis of Prodrug 1 (Peptide I-Melphalan)

Peptide I (SEQ ID NO 3): Tyr-Gly-Leu-Leu-Gly-Ile-Ala-Gly-Pro-Pro-Gly-Pro-Pro-Leu-Tyr-Lys-Lys-Ile-Ile-Lys-Lys-Leu-Leu-Gln-Ser was synthesized as described in Example 4 and then coupled to the drug.

t-Butoxycarbonyl-N-Melphalan (molar ratio 1:2 to peptide) was dissolved in DMF, and mixed for 5 minutes with the peptide-resin. TBTU (molar rate 1:1) was added for 5 minutes and DIPEA (molar ratio 2:1) was added. Coupling of t-Butoxycarbonyl-N-Melphalan to peptide-resin was made for 2-24 hours at room temperature with mechanical mixing and nitrogen bubbling. The coupling was monitored by spectroscopic measuring at 254 nm of the free t-Butoxycarbonyl-N-Melphalan in the reaction mixture.

At the end of the prodrug 1 synthesis cleavage and side chain deprotection of peptide-Melphalan was made as described in Example 4.

The peptide-Melphalan was analyzed using reversed-phase HPLC, mass spectrometry, and gel electrophoresis separation as described in Example 4.

EXAMPLE 8

Synthesis of Prodrug 2-Peptide I-Methotrexate

Peptide I (SEQ ID NO 3): Tyr-Gly-Leu-Leu-Gly-Ile-Ala-Gly-Pro-Pro-Gly-Pro-Pro-Leu-Tyr-Lys-Lys-Ile-Ile-Lys-Lys-Leu-Leu-Gln-Ser was synthesized as described in Example 4 and then coupled to the drug.

Di-t-Butoxycarbonyl-N-Methotrexate (molar ratio 1:1.2 to peptide) was dissolved in NMP, and mixed for 5 minutes with the peptide-resin. HBTU (molar ratio 1:1 to methotrexate) was added for 5 minutes and DIPEA (molar ratio 2:1 to methotrexate) was added. Coupling of methotrexate to peptide-resin was made for 2-24 hours at room temperature with mechanical mixing and nitrogen bubbling. The coupling was monitored by spectroscopic measuring at 302 nm of the free methotrexate in the reaction mixture.

At the end of the prodrug 2 synthesis, cleavage, and side chain deprotection of peptide-Methotrexate were carried out as described in Example 4.

The peptide-Methotrexate was analyzed using reversed-phase HPLC, mass spectrometry, and gel electrophoresis separation as described in Example 4.

EXAMPLE 9

Synthesis of Prodrug 3-Peptide I-Chlorambucil

Peptide I (SEQ ID NO 3): Tyr-Gly-Leu-Leu-Gly-Ile-Ala-Gly-Pro-Pro-Gly-Pro-Pro-Leu-Tyr-Lys-Lys-Ile-Ile-Lys-Lys-Leu-Leu-Gln-Ser was synthesized as described in Example 4 and then coupled to the drug.

Chlorambucil (molar ratio 1:2 to peptide) was dissolved in NMP, and mixed for 5 minutes with the peptide-resin. HBTU (molar ratio 1:1 to chlorambucil) was added for 5 minutes and DIPEA (molar rate 2:1 to chlorambucil) was added. Coupling of chlorambucil to peptide-resin was made for 2-24 hours at room temperature with mechanical mixing and nitrogen bubbling. The coupling was monitored by spectroscopic measuring at 263 nm of the free chlorambucil in the reaction mixture. At the end of the peptide-drug synthesis the resin was washed for 5 times with NMP, and 10 times with DCM on cinder glass. Cleavage of the drug from the resin was carried out by 90% TFA containing 5% H2O and 5% triisopropylsilan for 3 hours under mixing at room temperature. The drug was worked-up using process 4.

The peptide-Chlorambucil was analyzed using reversed-phase HPLC, mass spectrometry, and gel electrophoresis separation as described in Example 4.

EXAMPLE 10

Synthesis of Prodrug 4-Peptide I-Folic Acid

Peptide I (SEQ ID NO 3) was synthesized as described in Example 4 and then coupled to folic acid. Folic acid was dissolved in DMF for 3 minutes, reactivated with PyBOP (molar ratio 1:1.3 to acid) for 3 minutes. DIPEA (molar rate 2:1 to acid) was added and the mixture was transferred to the peptide-resin. Coupling of folic acid to peptide-resin was made for 120 minutes at room temperature with mechanical mixing and nitrogen bubbling.

Cleavage and analysis of peptide-folic acid was carried our as described in example 8.

EXAMPLE 11

Synthesis of Prodrug 5-Peptide I-N—N'-Diethylaminobenzoic Acid

Peptide I (SEQ ID NO 3) was synthesized as described in Example 4 and then coupled to N—N'-Diethylaminobenzoic acid.

N—N'-Diethylaminobenzoic acid (molar ratio 1:2 to peptide) was dissolved in NMP, and mixed for 5 minutes with peptide-resin. HBTU (molar ratio 1:1 was added for 5 minutes and DIPEA (molar rate 2:1 was added. Coupling of N—N'-Diethylaminobenzoic acid to peptide-resin was made for 2-24 hours at room temperature with mechanical mixing and nitrogen bubbling. The coupling was monitored by spectroscopic measuring at 263 nm of the free N—N'-Diethylaminobenzoic in the reaction mixture.

Cleavage and analysis of peptide-N—N'-Diethylaminobenzoic was carried out as described in example 9.

EXAMPLE 12

Synthesis of Prodrug 6-Peptide II-Chlorambucil

Synthesis of the peptide carrier II (SEQ ID NO 6): Ser-Pro-Gly-Arg-Val-Val-Arg-Gly-Lys-Gly-Lys-Gly-Gln-Lys-Arg-Lys-Arg-Lys-Lys-Ser-Arg-Tyr-Lys-Ser-Trp-Ser-Val was synthesized as described in Example 5 and then coupled to Chlorambucil as described in example 9.

Cleavage and analysis of peptide-chlorambucil was carried out as described in example 9.

EXAMPLE 13

Synthesis of Prodrug 7-Peptide III-Melphalan

Synthesis of the peptide carrier II (SEQ ID NO 8): Val-Arg-Gly-Lys-Gly-Lys-Gly-Gln-Lys-Arg-Lys-Arg-Lys-Lys-Ser-Arg-Tyr-Lys-Ser-Trp-Ser-Val was synthesized as described in Example 6 and then coupled to Melphalan as described in example 7.

Cleavage and analysis of peptide-Melphalan was carried out as described in example 6.

EXAMPLE 14

Synthesis of Legumain Cleavable Prodrug 8

A. Synthesis of Legumain Cleavable Peptide: Pro-Thr-Asn

The peptide cleavable by legumain is synthesized by using combinatorial chemistry and solid or liquid phase peptide synthesis. Fmoc/Boc protected amino acids are used for the synthesis.

The first amino acid Fmoc-Asn(Trt)-OH is coupled to Wang resin by using Dichlorobenzoylchloride method as described in example 4.

The next amino acids are bound to the peptide-resin by subsequent steps of deprotection and coupling. Aat the end of peptide synthesis, cleavage of the peptide from the resin is performed by using TFA as described in example 4.

The peptide is analyzed using reversed-phase HPLC, mass spectrometry, and spectrophotometer.

B. Synthesis of Boc-Pro-Thr-Asn-MTX

The peptide Pro-Thr-Asn is protected with Boc using di-tert-butylcarbonate method as described in example 1. Boc protected peptide is coupled to methotrexate (MTX) using DIC as follows: Boc-Pro-Thr-Asn is dissolved in DMF, DIC is added (molar ratio 1:1) and mixed for 30 minutes. Solid methotrexate is added to the mixture (molar ratio 1:1 drug:peptide) and incubated for 24 hours at room temperature with mixing. The DMF is evaporated and the product is precipitated and washed with tert-Butyl-Methyl-Ether.

C. Synthesis of Pro-Thr-Asn-MTX

Cleavage of the Boc group is carried out by 90% TFA containing 5% H2O for 3 hours under mixing at room temperature. The Thr-Thr-Asn-MTX is analyzed using reversed-phase HPLC and mass spectrometry as described in Example 4. Pro-Thr-Asn-Methotrexate gives solid yellowish powder with molecular mass of 766 g/mol.

EXAMPLE 15

Synthesis of Legumain Cleavable Prodrug 9

A. Synthesis of Legumain cleavable peptide: Thr-Thr-Asn-Leu

The peptide cleavable by legumain is synthesized as described in example 14.

B. Synthesis of Fmoc-Thr-Thr-Asn-Leu-Doxorubicin

The peptide is protected with Fmoc using 9-fluorenyl-methel-succinimidyl-carbonate method as described in example 2. The Fmoc protected peptide is coupled to Doxorubicin using DIC as described in example 14.

C. Synthesis of Thr-Thr-Asn-Leu-Doxorubicin

Deprotection of the Fmoc group is carried out by 20% piperidin in DMF for 30 minutes with mixing at room temperature. The Thr-Thr-Asn-Leu-Doxorubicin is analyzed using reversed-phase HPLC and mass spectrometry as described in Example 4. The product gives solid powder with molecular mass of 989 g/mol.

EXAMPLE 16

Synthesis of Legumain Cleavable Prodrug 10

A. Synthesis of Legumain Cleavable Peptide: Asn-Lys

The peptide cleavable by legumain was synthesized as described in example 4. The first amino acid Fmoc-Lys(Mtt)-OH was coupled to Wang resin by using Dichlorobenzoyl-chloride method as described in example 4.

Boc-Asn(Trt)-OH was bound to the peptide-resin by subsequent steps of deprotection and coupling. The Lys protecting group Mtt was removed with 1% TFA in DCM and monitored by O.D. at 460 nm.

B. Synthesis of Asn-Lys(Acetyl-5-Fluorouracil)

The drug 5-Fluorouracil-1-Acetic acid was coupled to peptidyl resin with DIC/HOBT in DMF. The resin was washed with DMF and DCM. Cleavage of peptide-drug was carried out by TFA with 10% $H_2O$. The TFA was evaporated and the product was precipitated and washed with tert-Butyl-Methyl-Ether.

The Asn-Lys(Acetyl-5-Fluorouracil) was analyzed using reversed-phase HPLC and mass spectrometry as described in Example 4.

EXAMPLE 17

Tissue Culture Analysis of the Drug Combination

Human umbilical vein-derived endothelial cells (HUVEC) were prepared from umbilical veins and cultured as described previously. The HUVE cells were grown in M199 medium supplemented with 20% fetal calf serum, vitamins, 1 ng/ml hbFGF, and antibiotics.

Human melanoma cells (WW-94) were grown in 50% DMEM/50% F-12 medium supplemented with 10% fetal calf serum and antibiotics.

Human Breast cancer cells (MCF-7) were grown in DMEM medium supplemented with 10% fetal calf serum and antibiotics.

To determine the biological activity of the drugs, HUVEC (normal cells) or melanoma (cancer) cells were seeded in 24-well dish at a concentration of 10,000-20,000 cells/well, and increasing concentrations of the prodrug 3-Peptide I-Chlorambucil (P-CAC) were added to the wells. As controls, either Chlorambucil or the peptide carrier was added under the same experimental conditions. After 72 hours the cells were washed with phosphate buffer saline (PBS), suspended with 0.5% EDTA/PBS, and counted using cell coulter (Electronics ZM). Cell viability was verified by trypan-blue staining and hemocytometer analysis. IC50 indicates the concentration of the drug measured at 50% of the cell death.

Figure 4A:
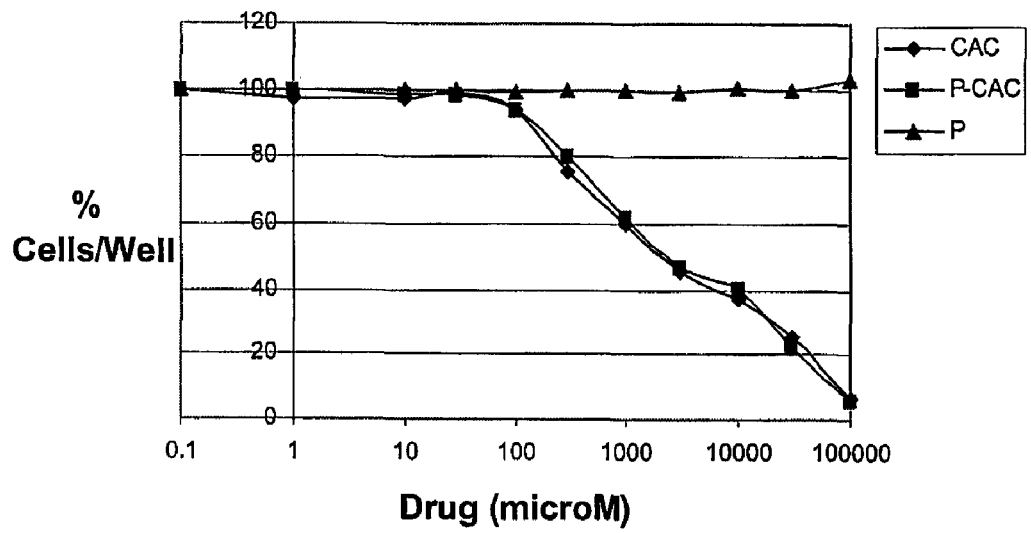
FIG. 4A-B shows a comparison between cancer and normal cell death at increasing concentrations of the prodrug 3.
Figure 4B:
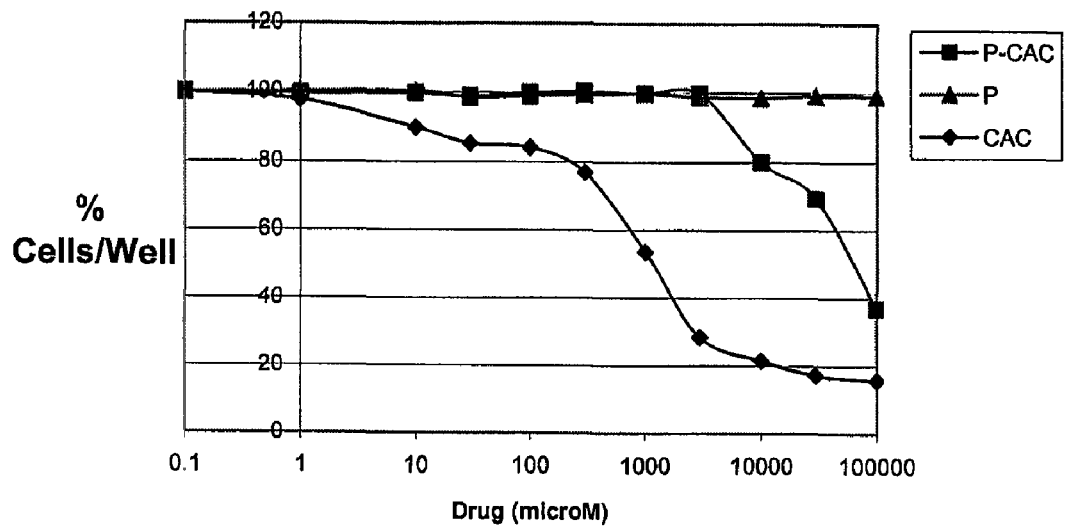

FIG. 4 shows that the peptide carrier is not toxic either to the HUVEC or to melanoma cells. Chlorambucil is very toxic both to cancer and normal cells (IC50 is 2 mM). The prodrug Peptide I-Chlorambucil is efficient as a chemotherapeutic agent in killing cancer cells with an IC50 of 2 mM (FIG. 4A). However, this prodrug is much less toxic to HUVE cells (IC50 of 60 mM)(FIG. 4B), i.e., 30 times less toxic to normal cells.

EXAMPLE 18

MTT Assay for Estimation of the Toxicity of the Drugs

HUVEC or melanoma cells were seeded in 96-well ELISA dish at a concentration of 10,000-20,000 cells/well, and various concentrations of the prodrug 1 were added to the wells as described in Example 17. As a control, Melphalan was added under the same experimental conditions. After 72 hours the medium was aspirated, and DMEM containing 5% FCS and 0.5 mg/ml MTT (an indicator of cell viability) was added. The cells were incubated for 2-4 hours at 37° C. and 5% CO2. At the end of the incubation the cells were washed with phosphate buffer saline (PBS), and dissolved with DMSO. The results were analysed using Techan ELISA reader equipped with a 570 nm filter.

Figure 5A:
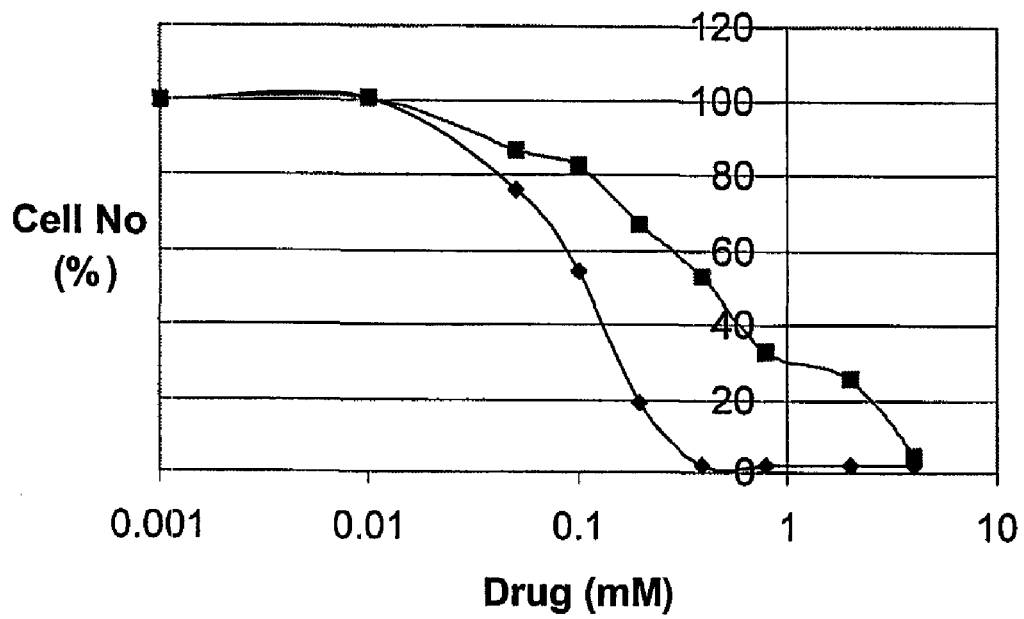
FIG. 5A-B depicts a comparison between normal and cancer cells death at increasing concentrations of the prodrug 1.
Figure 5B:
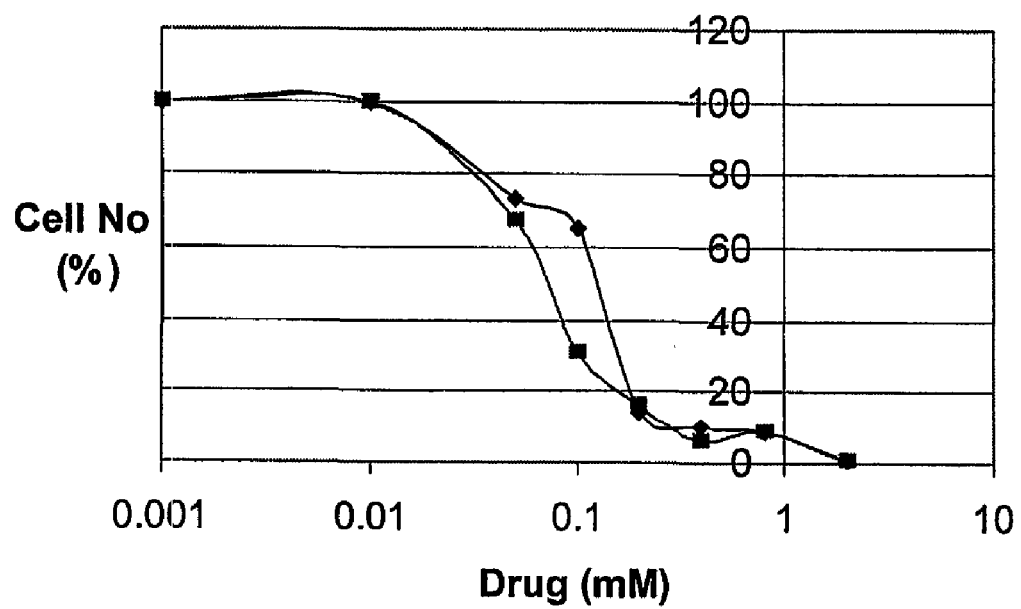

FIG. 5 shows that Melphalan (♦) kills efficiently both cancer and normal cells. It also shows that the prodrug Peptide I-Melphalan (■) is as efficient as the Melphalan itself in killing cancer cells (FIG. 5B), but it is less toxic to normal cells (FIG. 5A). The IC50 for Melphalan in HUVE cells and in melanoma cells is 0.1 mM, and 0.07 mM, respectively. The IC50 for the prodrug 1 in HUVE cells and in melanoma cells is 0.5 mM and 0.07 mM, respectively. These results show that this prodrug of Melphalan is 7 times less toxic to normal cells.

EXAMPLE 19

In-vitro Release of the Methotrexate from Peptide I-Methotrexate

To find out whether proteases are secreted to the conditioned medium of cancer cells, breast cancer cells or melanoma cells were grown to sub-confluence in a 10 cm dish. The cells were washed with PBS, and further incubated with serum free medium. HUVE cells were grown to confluence at 10 cm dish. The cells were washed with M-199 medium, and conditioned with M-199 with 1% heat inactivated serum. The conditioned medium was collected after 24 hours.

In-vitro release of Methotrexate from the peptide I-Methotrexate was carried out in a liquid phase. The prodrug was dissolved in PBS, and incubated for up to 4 hours at 37° C. in the absence or presence of the cancer cells or HUVE cells (normal cells) conditioned medium. The release of the Methotrexate from the peptide I-Methotrexate was monitored by spectroscopic measuring of the free Methotrexate at 302 nm.

EXAMPLE 20

In-vitro Release of the Melphalan from Peptide III-Melphalan

In-vitro release of Melphalan from the peptide III-Melphalan was carried out in a liquid phase as described in Example 19. The drug was dissolved in PBS and incubated for 3 hours at 37° C. in the absence or presence of cancer cells or normal cells conditioned medium. The release of the Melphalan from the peptide III-Melphalan was monitored by spectroscopic measuring of the free Melphalan at 254.

EXAMPLE 21

In-vitro Release of the Chlorambucil from the Peptide I-Chlorambucil

In-vitro release of Chlorambucil from the peptide carrier was carried out in a liquid phase as described in Example 19. Peptide I-Chlorambucil was dissolved in PBS, and incubated for 2 hours at 37° C. in the absence or presence of purified MMPs, or in the presence of conditioned medium of either human melanoma cells (HMCM) or human breast cancer cells (BCCM). To show that the GAGs can modulate the release of the chemotherapeutic agent from the peptide carrier the 2 hours incubation mentioned above was carried out in the absence or presence of 10 µg/ml heparin.

At the end of the incubation the reaction mixture was incubated with heparin-sepharose (30 minutes at 0° C.). The supernatant was collected, and the release of free chlorambucil was monitored by spectrophotometer at a wavelengh of 305 nm.

Figure 6:
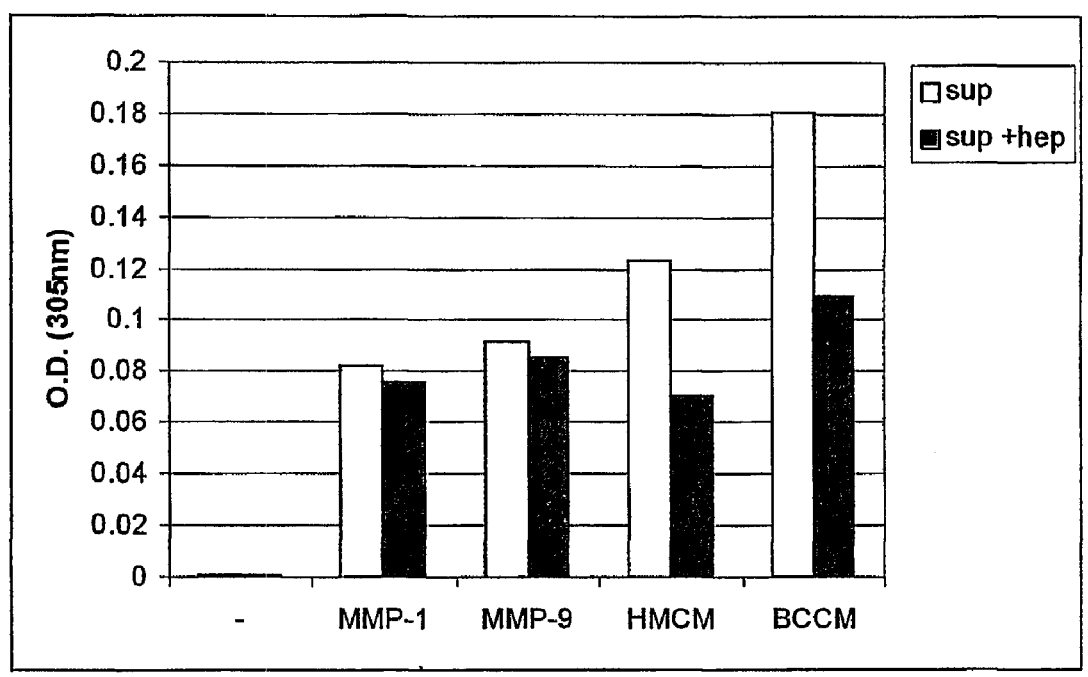
FIG. 6 shows an in-vitro release of Chlorambucil from its peptide carrier (prodrug 3) by purified MMPs, or by the cancer cell conditioned medium.

FIG. 6 shows that the chemotherapeutic agent can be released from the peptide carrier either by purified MMPs, or by MMPs secreted by cancer cells.

Addition of heparin to the reaction mixture inhibited the release of the chemotherapeutic agent from the peptide carrier, suggesting that GAGs can modulate the drug activity. For example, native proteoglycans such as Serglycin can be used as a carrier for the drug, protecting it from degradation.

EXAMPLE 22

In adult nude mice the following procedures are carried out under general anesthesia (Ketamin 1 mg/10 g b.w.+0.01 mg/10 g b.w.):
A. A chronic I.V. access is opened by inserting a catheter to the jugular vein.
B. S.C. Injection of 100 µl volume of human cancer cell suspension in normal saline containing $1 \times 10^6$ cells. Tumor xenografts proliferate within 2-6 weeks in order to reach predetermined average size. The drugs are daily delivered by i.v. injections.

The pharmacological agents in use are prodrugs of Melphalan with doses of 40-150 mg/m$^2$ and prodrugs of Fluorouracil with doses of 300-450 mg/m$^2$.

EXAMPLE 23

Manufacture of a Medicament Containing Synthetic Peptides of the Invention

As used herein a "pharmaceutical composition" refers to a preparation of one or more of the prodrugs described herein, or physiologically acceptable salts thereof, with other chemical components such as physiologically suitable carriers and excipients. The purpose of a pharmaceutical composition is to facilitate administration of a compound to an organism.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Pharmaceutical compositions may also include one or more additional active ingredients, such as, but not limited to, conventional anti-migraine agents.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate. In addition enterocoating are useful as it is desirable to prevent exposure of the peptides of the invention to the gastric environment.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the peptides for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated.

Determination of a therapeutically effective amount is well within the capability of those skilled in the art, especially in light of the detailed disclosure provided herein.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, and all other relevant factors.

The following example is an illustration only of a method of treating a subject with a peptide according to the invention, in order to treat a pathological condition associated with a solid tumor or a related condition, and is not intended to be limiting.

The method includes the step of administering the prodrug, in a pharmaceutically acceptable carrier as described above, to a subject to be treated. The medicament is administered according to an effective dosing methodology, preferably until a predefined endpoint is reached, such as a reduction or amelioration of the pathological condition in the subject.

References

Bernfield, M., Kokenyesi, R., Kato, M., Hinkes, M. T., Spring, J., Gallo, R. L. and Lose, E. J. (1992) Annu Rev. Cell Biol. 8, 365-393.

Dano K, Behrendt N, Brünner N, Ellis V, Ploug M, Pyke C: Fibrinolysis 1994, 8: 189-203.

Fidler I. J. (1997) In: Devita V. T., et al. (Eds.) Cancer: Principles and Practice of Oncology (5th edn). (pp. 135-152): Lippincott-Raven.

Gitay-Goren, H., Soker, S., Vlodaysky, I. and Neufeld, G. (1992) J. Biol. Chem. 267, 6093-6098.

Kuefner, U., Lohrman, U., Montejano, Y. D., Vitols, K. S., and Hunnekens, F. M. (1989) Biochemistry 28: 2288-97.

Massova I. et al. (1998) FASEB J., 12, 1075-1095.

Menger et al. (1994) Bioconjugate Chem. 5, 162-166.

Poltorak, Z., Cohen, T., Sivan, R., Kandelis, Y., Spira, G., Vlodaysky, I., Keshet, E., and Neufeld, G. (1997) J. Biol. Chem. 272, 7151-7158.

Yamada, K. M. and Geiger, B. (1997) Curr. Opin. Cell Biol. 9, 76-85.

Yayon, A., M. Klagsbrun, J. D. Esko, P. Leder, and D. M. Ornitz (1991). Cell. 64: 841-848.

What is claimed is:

1. A prodrug comprising a conjugate of at least one antiproliferative drug molecule covalently coupled directly or via a linker to a peptide moiety, said peptide moiety being specifically cleavable by an asparaginyl protease abundant in or secreted by malignant cells, thereby preferentially releasing the antiproliferative drug molecule within or at the malignant cells by the cleaving action of the asparaginyl protease, wherein the asparaginyl protease is legumain.

2. The prodrug of claim 1, wherein the antiproliferative drug is selected from the group consisting of a cytotoxic, a cytostatic or a chemotherapeutic drug.

3. The prodrug of claim 1, wherein the conjugate is substantially pharmacologically inactive.

4. The prodrug of claim 1, wherein the antiproliferative drug is selected from the group consisting of alkylating agents, antimetabolites, antitumor antibiotics, vinca alkaloids, epipodophyllotoxins, nitrosoureas, hormonal and antihormonal agents, and toxins.

5. The prodrug of claim 1, wherein the antiproliferative drug is selected from the group consisting of: cyclophosphamide, chlorambucil, busulfan, Melphalan, Thiotepa, ifosphamide, Nitrogen mustard, methotrexate, 5-Fluorouracil, cytosine arabinoside, 6-thioguanine, 6-mercaptopurine, doxorubicin, daunorubicin, idarubicin, nimitoxantron, dactinomycin, bleomycin, mitomycin, plicamycin, epipodophyllotoxins vincrist, vinblastin, vindestin, Etoposide, Teniposide, carmustin, lomustin, semustin, streptozocin, adrenocorticorticoids, estrogens, antiestrogens, progestins, aromatase inhibitors, androgens, antiandrogens, dacarbazin, hexamethylmelamine, hydroxyurea, mitotane, procarbazide, cisplastin, and carboplatin.

6. The prodrug of claim 5, wherein the antiproliferative drug is selected from a group consisting of Melphalan, Methotrexate, Chlorambucil, Doxorubicin, and 5-fluorouracil.

7. The prodrug of claim 1, wherein the peptide cleavable by the asparaginyl protease consists of from two to about fourteen amino acids at least one of which is asparagine.

8. The prodrug of claim 1, wherein the peptide cleavable by legumain consists of two to about fourteen amino acids comprising the amino acid sequence X1-X2-X3, wherein X1 is selected from the group consisting of Pro, Thr, Asn, and Ala, X2 is selected from the group consisting of Thr, Pro, Asn, and Ala, and X3 is Asn.

9. The prodrug of claim 8, wherein the peptide cleavable by legumain is selected from the group consisting of SEQ ID NO:9 to SEQ ID NO:32.

10. The prodrug of claim 1 further comprising at least one protecting group capable of preventing digestion of the peptide moiety by nonspecific proteases.

11. The prodrug of claim 1 comprising a plurality of antiproliferative drug molecules.

12. The prodrug of claim 1, wherein the linker between the drug and the peptide comprises any chemical compound which may be removed chemically, enzymatically or which decomposes spontaneously.

13. The prodrug of claim 1, wherein the peptide cleavable by legumain consists of the amino acid sequence selected from the group consisting of SEQ ID NO:33 to SEQ ID NO:38 inclusive.

14. A pharmaceutical composition comprising as an active ingredient a prodrug according to claim 1 together with a pharmaceutically acceptable excipient or diluent.

15. A method of treating a subject suffering from a cancer malignancy comprising administering to the subject a therapeutically effective amount of a pharmaceutical composition according to claim 14.

16. The method of claim 15, wherein the pharmaceutical composition is administered intravenously.

17. A method for producing a prodrug, the method comprising the step of linking at least one antiproliferative drug molecule and a peptide moiety to form the prodrug of claim 1, with the peptide moiety being specifically cleavable by legumain abundant in or secreted by malignant cells.

18. The method of claim 17, wherein the antiproliferative drug is selected from the group consisting of alkylating agents, antimetabolites, antitumor antibiotics, vinca alkaloids, epipodophyllotoxins, nitrosoureas, hormonal and antihormonal agents, and toxins.

19. The method of claim 17, wherein the peptide moiety cleavable by legumain consists from two to about fourteen amino acids at least one of which is asparagine.

20. The prodrug of claim 1, wherein the antiproliferative drug is daunorubicin and the cleavable peptide is Pro-Thr-Asn as set forth in SEQ ID NO:9.

21. The method of claim 17, wherein the antiproliferative drug is daunorubicin and the cleavable peptide is Pro-Thr-Asn as set forth in SEQ ID NO:9.

* * * * *

SEQUENCE LISTING

```
<160> NUMBER OF SEQ ID NOS: 38

<210> SEQ ID NO 1
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 1

Pro Leu Tyr Lys Lys Ile Ile Lys Lys Leu Leu Gln Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 2

Tyr Gly Leu Leu Gly Ile Ala Gly Pro Pro Gly Pro
1               5                   10

<210> SEQ ID NO 3
<211> LENGTH: 25
<212> TYPE: PRT
<213> ORGANISM: Artificial Sequence
<220> FEATURE:
<223> OTHER INFORMATION: SYNTHETIC PEPTIDE

<400> SEQUENCE: 3

Tyr Gly Leu Leu Gly Ile Ala Gly Pro Pro Gly Pro Pro Leu Tyr Lys
1               5                   10                  15

Lys Ile Ile Lys Lys Leu Leu Gln Ser
            20                  25

<210> SEQ ID NO 4
<211> LENGTH: 19
<212> TYPE: PRT
<213> ORGANISM: Artificial Sequence
<220> FEATURE:
<223> OTHER INFORMATION: SYNTHETIC PEPTIDE
```

```
<400> SEQUENCE: 4

Lys Gly Lys Gly Gln Lys Arg Lys Arg Lys Lys Ser Arg Tyr Lys Ser
1               5                   10                  15

Trp Ser Val

<210> SEQ ID NO 5
<211> LENGTH: 8
<212> TYPE: PRT
<213> ORGANISM: Artificial Sequence
<220> FEATURE:
<223> OTHER INFORMATION: SYNTHETIC PEPTIDE

<400> SEQUENCE: 5

Ser Pro Gly Arg Val Val Arg Gly
1               5

<210> SEQ ID NO 6
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 6

Ser Pro Gly Arg Val Val Arg Gly Lys Gly Lys Gly Gln Lys Arg Lys
1               5                   10                  15

Arg Lys Lys Ser Arg Tyr Lys Ser Trp Ser Val
                20                  25

<210> SEQ ID NO 7
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 7

Val Arg Gly
1

<210> SEQ ID NO 8
<211> LENGTH: 22
<212> TYPE: PRT
<213> ORGANISM: Artificial Sequence
<220> FEATURE:
<223> OTHER INFORMATION: SYNTHETIC PEPTIDE

<400> SEQUENCE: 8

Val Arg Gly Lys Gly Lys Gly Gln Lys Arg Lys Arg Lys Lys Ser Arg
1               5                   10                  15

Tyr Lys Ser Trp Ser Val
                20

<210> SEQ ID NO 9
<211> LENGTH: 3
<212> TYPE: PRT
<213> ORGANISM: Artificial Sequence
<220> FEATURE:
<223> OTHER INFORMATION: SYNTHETIC PEPTIDE

<400> SEQUENCE: 9

Pro Thr Asn
1

<210> SEQ ID NO 10
```

```
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 10

Pro Asn Asn
1

<210> SEQ ID NO 11
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 11

Pro Ala Asn
1

<210> SEQ ID NO 12
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 12

Pro Pro Asn
1

<210> SEQ ID NO 13
<211> LENGTH: 3
<212> TYPE: PRT
<213> ORGANISM: Artificial Sequence
<220> FEATURE:
<223> OTHER INFORMATION: SYNTHETIC PEPTIDE

<400> SEQUENCE: 13

Thr Thr Asn
1

<210> SEQ ID NO 14
<211> LENGTH: 3
<212> TYPE: PRT
<213> ORGANISM: Artificial Sequence
<220> FEATURE:
<223> OTHER INFORMATION: SYNTHETIC PEPTIDE

<400> SEQUENCE: 14

Thr Asn Asn
1

<210> SEQ ID NO 15
<211> LENGTH: 3
<212> TYPE: PRT
<213> ORGANISM: Artificial Sequence
<220> FEATURE:
<223> OTHER INFORMATION: SYNTHETIC PEPTIDE

<400> SEQUENCE: 15

Thr Ala Asn
1

<210> SEQ ID NO 16
<211> LENGTH: 3
<212> TYPE: PRT
```

```
<213> ORGANISM: Artificial Sequence
<220> FEATURE:
<223> OTHER INFORMATION: SYNTHETIC PEPTIDE

<400> SEQUENCE: 16

Thr Pro Asn
1

<210> SEQ ID NO 17
<211> LENGTH: 3
<212> TYPE: PRT
<213> ORGANISM: Artificial Sequence
<220> FEATURE:
<223> OTHER INFORMATION: SYTNHETIC PEPTIDE

<400> SEQUENCE: 17

Asn Thr Asn
1

<210> SEQ ID NO 18
<211> LENGTH: 3
<212> TYPE: PRT
<213> ORGANISM: Artificial Sequence
<220> FEATURE:
<223> OTHER INFORMATION: SYNTHETIC PEPTIDE

<400> SEQUENCE: 18

Asn Asn Asn
1

<210> SEQ ID NO 19
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 19

Asn Ala Asn
1

<210> SEQ ID NO 20
<211> LENGTH: 3
<212> TYPE: PRT
<213> ORGANISM: Artificial Sequence
<220> FEATURE:
<223> OTHER INFORMATION: SYNTHETIC PEPTIDE

<400> SEQUENCE: 20

Asn Pro Asn
1

<210> SEQ ID NO 21
<211> LENGTH: 3
<212> TYPE: PRT
<213> ORGANISM: Artificial Sequence
<220> FEATURE:
<223> OTHER INFORMATION: SYNTHETIC PEPTIDE

<400> SEQUENCE: 21

Ala Thr Asn
1

<210> SEQ ID NO 22
<211> LENGTH: 3
<212> TYPE: PRT
<213> ORGANISM: Artificial Sequence
<220> FEATURE:
```

<223> OTHER INFORMATION: SYNTHETIC PEPTIDE

<400> SEQUENCE: 22

Ala Asn Asn
1

<210> SEQ ID NO 23
<211> LENGTH: 3
<212> TYPE: PRT
<213> ORGANISM: Artificial Sequence
<220> FEATURE:
<223> OTHER INFORMATION: SYNTHETIC PEPTIDE

<400> SEQUENCE: 23

Ala Ala Asn
1

<210> SEQ ID NO 24
<211> LENGTH: 3
<212> TYPE: PRT
<213> ORGANISM: Artificial Sequence
<220> FEATURE:
<223> OTHER INFORMATION: SYNTHETIC PEPTIDE

<400> SEQUENCE: 24

Ala Pro Asn
1

<210> SEQ ID NO 25
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 25

Thr Thr Asn Leu
1

<210> SEQ ID NO 26
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 26

Thr Thr Asn Ala
1

<210> SEQ ID NO 27
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 27

Pro Thr Asn Leu
1

<210> SEQ ID NO 28
<211> LENGTH: 4
<212> TYPE: PRT
<213> ORGANISM: Artificial Sequence
<220> FEATURE:
<223> OTHER INFORMATION: SYNTHETIC PEPTIDE

```
<400> SEQUENCE: 28

Pro Thr Asn Ala
1

<210> SEQ ID NO 29
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 29

Pro Asn Asn Leu
1

<210> SEQ ID NO 30
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 30

Pro Asn Asn Ala
1

<210> SEQ ID NO 31
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 31

Thr Asn Asn Leu
1

<210> SEQ ID NO 32
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 32

Thr Asn Asn Ala
1

<210> SEQ ID NO 33
<211> LENGTH: 2
<212> TYPE: PRT
<213> ORGANISM: Artificial Sequence
<220> FEATURE:
<223> OTHER INFORMATION: SYNTHETIC PEPTIDE

<400> SEQUENCE: 33

Asn Lys
1

<210> SEQ ID NO 34
<211> LENGTH: 2
<212> TYPE: PRT
<213> ORGANISM: Artificial Sequence
<220> FEATURE:
<223> OTHER INFORMATION: SYNTHETIC PEPTIDE

<400> SEQUENCE: 34
```

```
Asn Leu
1

<210> SEQ ID NO 35
<211> LENGTH: 2
<212> TYPE: PRT
<213> ORGANISM: Artificial Sequence
<220> FEATURE:
<223> OTHER INFORMATION: SYNTHETIC PEPTIDE

<400> SEQUENCE: 35

Asn Ala
1

<210> SEQ ID NO 36
<211> LENGTH: 2
<212> TYPE: PRT
<213> ORGANISM: Artificial Sequence
<220> FEATURE:
<223> OTHER INFORMATION: SYNTHETIC PEPTIDE

<400> SEQUENCE: 36

Asn Glu
1

<210> SEQ ID NO 37
<211> LENGTH: 2
<212> TYPE: PRT
<213> ORGANISM: Artificial Sequence
<220> FEATURE:
<223> OTHER INFORMATION: SYNTHETIC PEPTIDE

<400> SEQUENCE: 37

Asn Asp
1

<210> SEQ ID NO 38
<211> LENGTH: 2
<212> TYPE: PRT
<213> ORGANISM: Artificial Sequence
<220> FEATURE:
<223> OTHER INFORMATION: SYNTHETIC PEPTIDE

<400> SEQUENCE: 38

Asn Asn
1
```